United States Patent [19]

Blades et al.

[11] Patent Number: 5,047,212

[45] Date of Patent: * Sep. 10, 1991

[54] INSTRUMENT FOR MEASUREMENT OF THE ORGANIC CARBON CONTENT OF WATER

[75] Inventors: Frederick K. Blades, Boulder; Richard D. Godec, Erie, both of Colo.

[73] Assignee: Anatel Corporation, Boulder, Colo.

[*] Notice: The portion of the term of this patent subsequent to Sep. 19, 2006 has been disclaimed.

[21] Appl. No.: 270,451

[22] Filed: Nov. 7, 1988

Related U.S. Application Data

[63] Continuation of Ser. No. 938,634, Feb. 9, 1987, abandoned, which is a continuation of Ser. No. 635,551, Aug. 2, 1984, Pat. No. 4,666,860, which is a continuation-in-part of Ser. No. 569,678, Jan. 10, 1984, Pat. No. 4,626,413.

[51] Int. Cl.$^5$ .............................................. G01N 31/12
[52] U.S. Cl. ............................... 422/82.02; 422/82.12; 422/78; 422/80; 422/186.3; 436/146
[58] Field of Search ............................... 422/68, 78–80, 422/82.02, 82.12, 186.3; 436/62, 146, 150; 250/372, 373, 435; 356/51

[56] References Cited

U.S. PATENT DOCUMENTS

| | | | |
|---|---|---|---|
| 2,019,871 | 11/1935 | Pettingill et al. | 436/52 |
| 3,224,837 | 12/1965 | Moyat . | |
| 3,287,088 | 11/1966 | Seevers . | |
| 3,535,087 | 10/1970 | Hart et al. . | |
| 3,607,071 | 9/1971 | Staflin et al. . | |
| 3,738,812 | 6/1973 | Berry . | |
| 3,854,877 | 12/1974 | Csaky et al. . | |
| 3,955,924 | 5/1976 | Northmore et al. . | |
| 3,958,941 | 5/1976 | Regan . | |
| 3,964,868 | 6/1976 | DiCola et al. . | |
| 4,140,018 | 2/1979 | Maldarelli . | |
| 4,227,151 | 10/1980 | Ellis et al. . | |
| 4,248,598 | 2/1981 | Blunck | 436/146 |
| 4,272,679 | 6/1981 | Blades . | |
| 4,288,229 | 9/1981 | Mar | 436/146 |
| 4,293,522 | 10/1981 | Winkler . | |
| 4,304,996 | 12/1981 | Blades . | |
| 4,357,668 | 11/1982 | Schwartz et al. . | |
| 4,418,566 | 12/1983 | Beck et al. . | |
| 4,523,331 | 6/1985 | Asija . | |
| 4,566,077 | 1/1986 | Zwicke . | |
| 4,683,435 | 7/1987 | Blades | 324/442 |
| 4,749,657 | 6/1988 | Takahashi et al. | 436/146 |
| 4,868,127 | 9/1989 | Blades et al. | 436/146 |

FOREIGN PATENT DOCUMENTS 3223167 12/1983 Fed. Rep. of Germany .
2029015 3/1980 United Kingdom .

OTHER PUBLICATIONS

Poirier et al., "A New Approach to the Measurement of Organic Carbon," American Laboratory, Dec. 1978, pp. 1–8.

Sybron brochure, PHOTOchem Organic Carbon Analyzers, Analytical Products, Boston, Mass.

Primary Examiner—David L. Lacey
Assistant Examiner—Jeffrey R. Snay
Attorney, Agent, or Firm—Michael de Angeli

[57] ABSTRACT

Apparatus for measurement of total organic carbon content of water, particularly of low relative organic content, is described which features a single sample cell for exposure of a static sample to ultraviolet radiation comprising electrodes for measuring the conductivity of the water. The conductivity is monitored as a function of time and the second time derivative of the conductivity signal is monitored to indicate when the oxidation reaction has been completed. Compensation for the contribution to conductivity of the water sample made by the instrument is achieved by subtracting a quantity porportional to the first time derivative of the conductivity at a time when the second time derivative reaches zero, indicating that the oxidation reaction is complete, from the change in the total conductivity measurement, the remainder being equal to the contribution to conductivity made by oxidation of the organic content of the water.

17 Claims, 11 Drawing Sheets

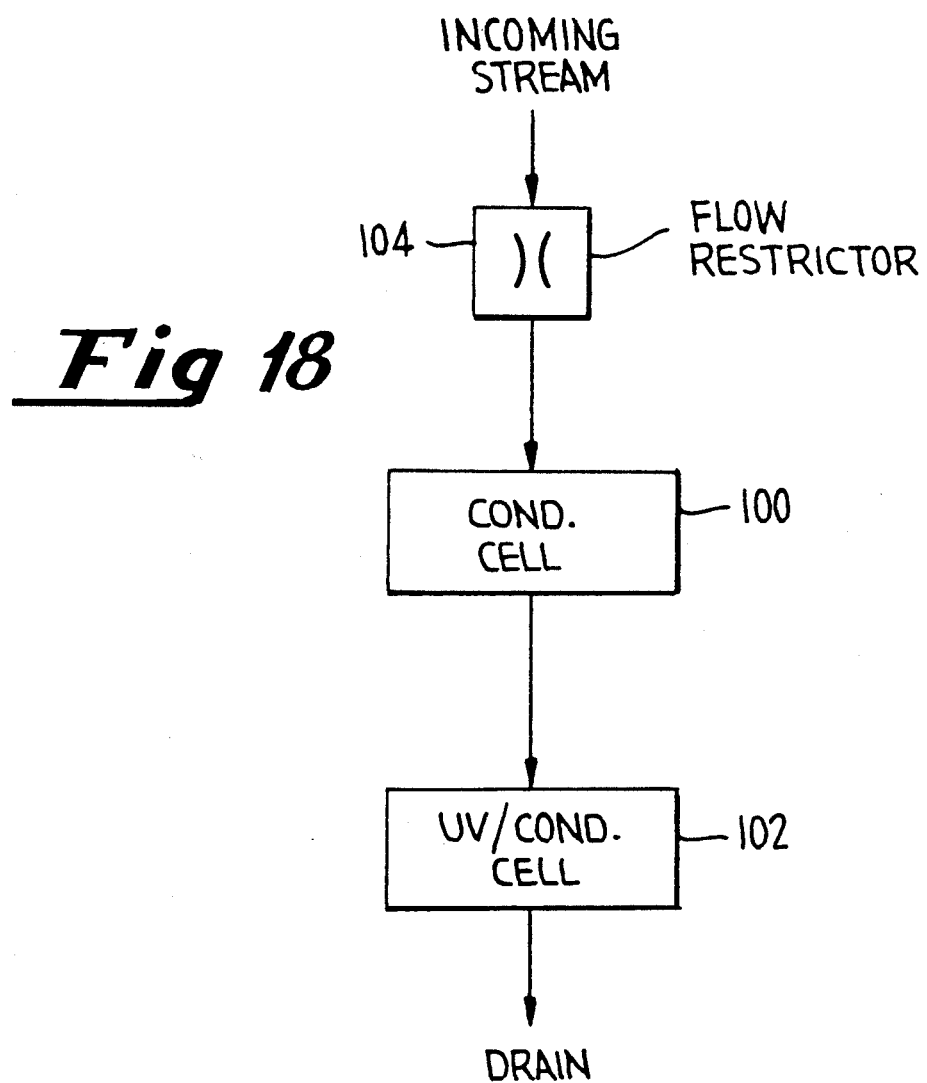

INSTRUMENT FOR MEASUREMENT OF THE ORGANIC CARBON CONTENT OF WATER

CROSS REFERENCE TO RELATED APPLICATIONS

This application is a continuation of Ser. No. 938,634, filed Feb. 09, 1987, now abandoned, which is a continuation of Ser. No. 635,551, filed Aug. 02, 1984, now U.S. Pat. No. 4,666,860, which is a continuation-in-part of Ser. No. 569,678, filed Jan. 10, 1984, now U.S. Pat. No. 4,626,413.

FIELD OF THE INVENTION

This invention relates to instruments for the measurement of the total organic carbon (TOC) content in water. More particularly, the invention relates to instruments for accurately measuring low levels of organic carbon in pure or ultrapure water streams.

BACKGROUND AND OBJECTS OF THE INVENTION

Modern high technology manufacturing processes often use highly purified "ultrapure" water in large quantities. The semiconductor industry in particular uses ultrapure water as a universal solvent in virtually every step of the production of integrated circuits. In recent years, it has been recognized that even trace amounts of organic contamination in the water, though often undetectable by the commonly-used ionic (i.e. conductivity-based) measurement techniques can severely degrade both product quality and yield. Accurate and continuous monitoring of the total organic content is crucial if these problems are to be avoided. Similar problems exist through other industries, such as pharmaceutical and chemical manufacturing.

Several prior art approaches to measurement of the organic content of water have been proposed. Those relevant to the present invention are primarily concerned with oxidation of the carbon in the organic material to carbon dioxide and then measuring the carbon dioxide content. This has been done in the past in several ways. The fact that carbon dioxide is an absorber of infrared light has been utilized. The oxidation has also been performed in several ways, including combustion, and using chemical oxidizers such as perchlorates. These methods are clumsy and are replete with the potential for significant errors, particularly in the low-TOC area addressed by the present invention. More relevant to the present invention is the approach shown in U.S. Pat. No. 3,958,941 to Regan, in which ultraviolet light is used to oxidize the carbon-containing organics to carbon dioxide. The carbon dioxide is then transported to a pure water sample, and the change in conductivity of the pure water due to the presence of the additional ionic species is monitored to determine the amount of organic material thus oxidized. Oxidation of the organics to $CO_2$ and measurement of the change in the water's conductivity are used by the apparatus of the present invention. However, several improvements over the Regan apparatus are shown herein.

The Regan apparatus, which is commercially available, is proposed as a tool for measuring organic content of water over a wide range, from the parts per million (ppm) range through parts per thousand and, indeed, even higher. Applicants have had experience with this apparatus, however, and find that the problems inherent in total organic carbon measurement at extremely low dissolved organic levels, on the order of one part per billion (ppb) to one ppm are such that a different type of apparatus should be used for these extremely low level measurements. Thus, while the Regan approach is workable, it is of primary utility in the areas of relatively high organic concentrations.

The Regan apparatus requires the operator to perform several independent preliminary measurement runs to determine the "instrument contribution" or background level of the instrument. The applicants have found that the values determined in such measurements tend to change with time, thereby requiring frequent "calibration" runs to maintain measurement accuracy.

It is therefore an object of the invention to provide a means whereby the instrument contribution can be accurately determined separately from the measured quantity, such that calibration runs are eliminated.

The Regan apparatus assumes a fixed time for the oxidation process to go to completion. If the organics present in the sample are difficult to oxidize, or if the ultraviolet lamp has aged so as to produce insufficient oxidizing radiation, they may not be completely oxidized in the time allotted, thus leading to misleadingly low measurements. Furthermore, if the level of organics is very low and oxidation proceeds to completion rapidly, the interference caused by instrument contribution may contribute significant errors.

It is therefore a further object of the invention to provide an instrument whereby the oxidation process can be monitored so that its actual completion can be accurately and readily determined.

As mentioned, the Regan apparatus provides a two-loop system, in which the organics in water are first oxidized by exposure to ultraviolet (UV) light, and the resulting carbon dioxide transferred to a measurement chamber, where it is dissolved in pure water, the conductivity of which is thereafter measured. The conductivity is thus measured in a different chamber than that in which the ultraviolet light is exposed to the water. This has the highly significant defect that transport of the carbon dioxide between the UV exposure chamber to the conductivity measurement chamber is obviously required. The present invention is designed to address measurement of the organic content of water in such low concentrations that any minor impurities which are added to the water by this or any comparable transport system (as well as loss of $CO_2$) can very greatly affect the accuracy of any measurement.

Accordingly, it is an object of the invention to provide an instrument for the measurement of total organic carbon in water which avoids water, $CO_2$ or other material handling or manipulative steps such that the impurities inevitably added in such steps are avoided.

The present invention overcomes the problems associated with the defects of the Regan apparatus due to its transport and manipulative step requirements by providing a single chamber in which the ultraviolet radiation is exposed to the water and in which the conductivity measurements are made. This has several advantages, among which are, of course, reduction of pollutants or contamination due to transport, simplicity and low cost. Furthermore, the fact that the electrodes can be and are in a preferred environment exposed directly to the UV light means that there is no or very little chance of organic fouling of the electrodes, another problem inherent in the Regan apparatus according to the two-chamber approach proposed thereby.

It is accordingly an object of the invention to provide an instrument for measurement of total organic carbon in water in which a static water sample is measured for background conductivity, is then exposed to ultraviolet light, and variation in its conductivity is measured over time, without movement from a single sample chamber, whereby inaccuracies due to manipulative steps are eliminated.

It is a further object of the invention to provide such an organic matter measurement instrument in which the electrodes used for conductivity measurement are directly exposed to the ultraviolet light used to oxidize the organic carbon to carbon dioxide, such that organic fouling of the electrodes is avoided.

It is a further object of the invention, in accordance with good design practice, to avoid use of materials in contact with the water sample which could lead to leaching of additional impurities, such as iron, polyethylene, and other materials found in the prior art designs, and instead to permit only relatively inert materials such as titanium or quartz to come into contact with the water sample.

As mentioned above, according to the invention, it is desired that a static water sample be examined; that is, according to the invention, a water sample is taken from the process of interest. The testing according to the invention is thus not an in-line process, as that term is typically used, although, in fact, the time taken for a typical measurement, on the order of one to twenty minutes, is such that substantially up-to-date information can be provided. (Note however that in some circumstances, detailed below, the apparatus of the invention can be used to monitor sudden changes in total organic carbon content in an in-line, real-time manner.) The prior art generally teaches away from such static measurements, because it is known that the materials comprising the electrodes used for the resistive measurements as well as those of the sample chamber tend to be leached out into the water stream and make some contribution to the conductivity of the water. The more delicate the measurement, the more serious these contributions can be. Use of a flowing water stream has been suggested to minimize the effects of such additional ions which alter the conductivity.

It is a further object of the invention to provide a means by which the instrument contribution or "background" conductivity can be accurately determined and subtracted from the total measured value for conductivity permitting use of a static sample measurement.

According to the present invention, accurate compensation is made for the instrument contribution due, e.g., to its materials leaching over time, so that the other advantages of static measurement can be realized, and so that the instrument contribution to conductivity, regardless of its source, is prevented from interfering with accurate measurement.

As mentioned, according to the process of the Regan patent, the conductivity of the water in a measurement chamber is first measured. The water sample of interest is exposed to ultraviolet light in a second exposure chamber for a fixed length of time. The carbon dioxide is then removed and dissolved into the water in the measurement chamber. The conductivity of the water is then measured and compared to its conductivity at the beginning of the exposure period. The difference is taken to be indicative of the change in conductivity due to $CO_2$ formed by oxidation of organic carbon. Because the relationship of conductivity of water to carbon dioxide content is known, this can be used to directly derive a measurement of organic carbon content. There are several difficulties inherent in this approach. One is that the background noise or instrument contribution, including the additional conductivity caused by leaching of organic or inorganic materials of the apparatus, is not repeatable over time, a fact brought out by the applicants' experiments. Furthermore, the dependence of conductivity of water on carbon dioxide content is not a linear function, but is exponential, such that at higher organic carbon contents, relatively little conductivity change is experienced with significant variation in organic carbon content. Hence, accurate determination of the background level is essential if an accurate measurement of organic content is to be provided.

Accordingly, it is an object of the invention to provide a method and instrument for measurement of the organic content of water in which accurate background compensation is made, yet in which background compensation is not dependent on repeatability of background measurement, and wherein compensation is made for any chemical activity of the sample chamber or apparatus caused by ultraviolet light, and wherein the compensation for background is sufficiently delicate that the precision of result necessary for distinguishing between conductivity caused by various relatively low amounts of organic content is made possible.

One primary difficulty with prior art TOC measuring instruments is that all presently available devices require frequent and tedious calibration, due largely to the high and somewhat varying instrument contribution or background.

Accordingly, it is an object of the invention to provide a TOC measuring instrument, the absolute calibration of which is made solely by correctly calibrating an integral temperature-corrected conductivity sensor.

It is a further object of the invention to provide a TOC measuring instrument which automatically detects and compensates for such spurious background, substantially eliminating the need for frequent calibration.

THE CONTINUATION-IN-PART APPLICATION

After filing of the parent application, it was realized that the sample cell design discussed therein had a number of defects. For one, the Teflon (trademark DuPont Corporation) material used for part of the cell deteriorates upon application of ultra-violet radiation. Further, the electrode design shown was not optimal with respect to uniformity of detection of ionic concentrations in the water sample. Additionally, it was desired to have the cell withstand higher pressures. Other aspects and improvements made by the second cell design will be explained below.

After the filing of the parent application it also became clear that in the case of certain oxidation reactions, intermediate products were being formed which had relatively higher conductivities than the ultimately-formed $CO_2$. This required modification of the data processing schemes employed to determine accurate TOC values.

Another discovery was that in monitoring the TOC content of a succession of water samples taken from the same process at intervals over a period of time, it is not always necessary to monitor the entire oxidation process, in order to arrive at an accurate result. This is because if the initial portion of the conductivity versus time curve closely tracks that of a previous sample, it can be assumed that the final portion of the curve will do likewise. This has permitted reduction of the time required to produce TOC output data.

Other aspects and objects of the improvements made according to the invention described in the present continuation-in-part application, will appear as the discussion proceeds. However, many of the aspects and objects of the original application remain; in particular, accurate total organic carbon determination through a simple, single sample evaluation. Similarly, it is desired that there be no transport or manipulative steps required, that no chemicals or other oxidizers be added to the sample, that the cell design be such that the electrodes are exposed to the ultraviolet light to prevent fouling, and that the system is capable of providing accurate TOC data with respect to a wide variety of sources of organic matter.

SUMMARY OF THE INVENTION

The present invention achieves the needs of the art and objects of the invention mentioned above by its provision of an instrument for the measurement of the total organic content of water. The instrument comprises a single sample cell with two electrodes exposed directly to incident ultraviolet light. The temperature-corrected conductivity of the water is measured to establish a background value with no incident UV light, and then the UV lamp is switched on, exposing the sample to oxidizing radiation. The temperature-corrected conductivity of the water is measured and recorded over time. In a preferred embodiment, a dedicated computer device is used to monitor changes in the conductivity of the water over time. The computer is used to separate the changes in conductivity due to production of $CO_2$ from changes due to background instrument contributions. The method of differentiation of conductivity caused by background contamination from oxidized organics producing $CO_2$ is based on the relative state of completion of the two processes.

In the case of oxidation the process is brought to completion within a short period of time, i.e., one to twenty minutes. It is therefore a substantially non-linear function, asymptotically approaching its final value in a relatively short period of time.

The background contamination, on the other hand, is to a degree a function of extremely small quantities of contaminants diffusing into the sample during the oxidation period, thus producing a gradual increase in sample conductivity not related to the production of $CO_2$. Since the level of contaminants diffusing during this oxidizing period is likely several orders of magnitude below saturation, the conductivity contribution during this time is substantially linear and can therefore be mathematically differentiated from the non-linear production of $CO_2$. Other mechanisms such as diffusion of the $CO_2$ away from the cell may also add to the instrument contribution; it appears that these too do not reach equilibrium in the relatively short period of time during which the oxidation reaction is completed, and are linear during that period. Differentiation between the linear instrument contribution and the non-linear oxidation contribution is accomplished by observing the second time derivative of the conductivity of the water. When the second derivative becomes zero, within a predetermined measurement accuracy limit, this indicates that the oxidation reaction has been completed.

The first time derivative of conductivity is also monitored; its value at the time the second derivative reaches zero is the "slope" of the background conductivity curve, due to the instrument contribution, and can be used to derive an indication of the total background noise, which can then be subtracted from the measured change in conductivity, such that the remainder is the conductivity resulting from the oxidation of the carbon present in the sample to $CO_2$.

According to the invention of the present continuation-in-part application, it is recognized that a third class of processes must be accounted for. This arises when the organic material in the water is a species which is oxidized to carbon dioxide only after passing through intermediate stages which have higher conductivity than the final product. Hence, means must be provided to identify such cases and to make accurate compensation. This can be done by monitoring the second time derivative of the conductivity curve in a matter generally similar to that previously defined.

It has also been realized that in cases of such relatively complex oxidation reactions, it may take as much as 15 to 20 minutes for the oxidation to be completed. While this is not in itself an insuperable obstacle to the utility of the apparatus of the invention, clearly it would be desirable to provide a shorter sampling period where possible. It has been realized that when monitoring the total organic carbon content of water samples from the same process stream taken at intervals over a period of time, the curves of the conductivity data versus time are essentially very similar from sample to sample, unless the total organic carbon content suddenly changes. Hence, it is possible to conclude with certainty that the final total organic carbon content value will be substantially the same as that derived in connection with previous samples, as long as where the departure of the initial conductivity values from those previously recorded is within a predetermined limit. This can be used to effectively speed up repetitive monitoring of the total organic carbon content.

BRIEF DESCRIPTION OF THE DRAWINGS

The invention will be better understood if reference is made to the accompanying drawings, in which:

FIG. 18 shows a device employing two cells in series.

DESCRIPTION OF THE PREFERRED EMBODIMENTS

Figure 1:
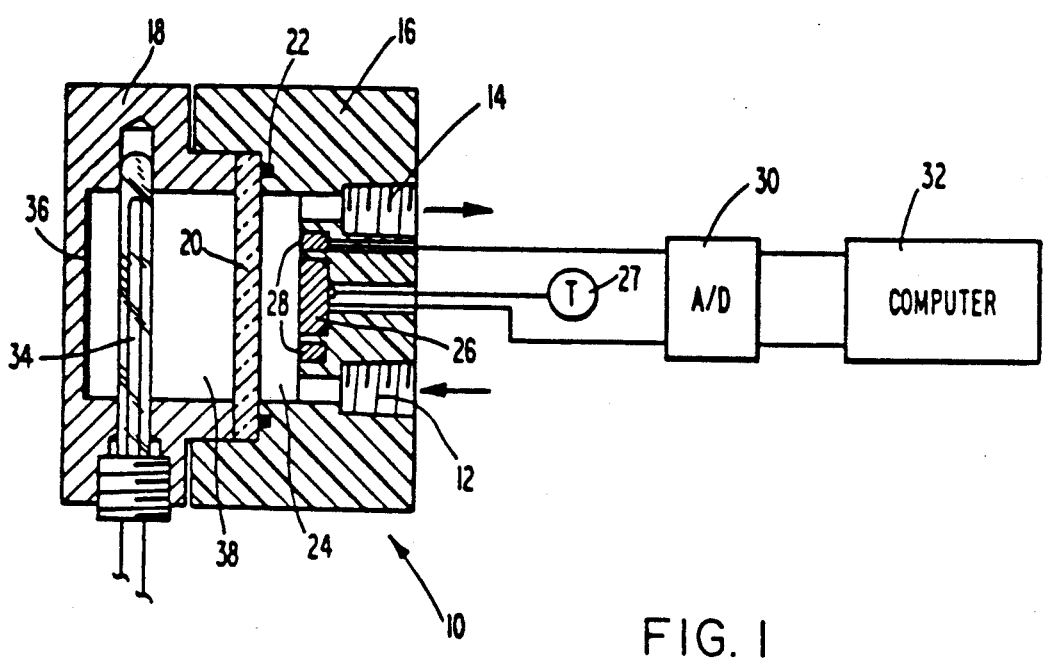
FIG. 1 shows a cross sectional view of the cell of the instrument according to the originally-preferred embodiment of the invention and shows schematically its connection to other parts of the apparatus.

A typical sample cell according to the originally preferred embodiment of invention is shown at 10 in FIG. 1. This cell is arranged to be connected at port 12 to a source of influent water, to be tested for the presence of organic carbon. The effluent water exits at port 14. Control valves (not shown) may be provided if necessary. In a high purity system, these may be of Teflon or similarly relatively inert materials. Typically, as noted, the process stream from which the water sample is taken may comprise such things as the water in a semiconductor processing line, pure water used in pharmaceutical manufacturing, organic chemical research, bioengineering, and other high precision laboratory and industrial operations.

The cell 10 comprises two main body portions 16 and 18. Body portion 16 is preferably formed of Teflon, ensuring that a minimal quantity of impurities are leached out into the water stream. A recess in the Teflon body 16 is covered by a quartz window 20, quartz also being an inert material, thus defining the sample chamber 24. In cases of high pressure systems, it may be necessary to take steps to limit the pressure on the window 20. Fastening devices such as screws (not shown) connecting the two body portions 16 and 18 compress the quartz window 20 into an O-ring 22, ensuring a fluid-tight chamber 24. Within the fluid-tight chamber 24 are disposed two concentric circular electrodes 26 and 28, respectively, which may in a preferred embodiment, be made of titanium, or another electrode material chosen for conductance to diffusion; palladium, iridium, rhodium and platinum are some possible alternatives. In the preferred embodiment, the electrodes may be chamfered as shown, and are an interference fit within the Teflon body portion 16, ensuring a good seal therebetween. The concentric electrode arrangement has several advantages. Chief among these is that the cell constant of this arrangement is quite high, ensuring relative sensitivity of the instrument to changes in conductance, whereas the capacitance between the two elements 26 and 28 is relatively low. As shown, the electrodes fit flush to the wall of the chamber; this discourages the formation of bubbles, fouling, and the like. A conventional temperature sensor 27 can conveniently be attached to the rear of the central electrode 26; this is used to compensate for variation in sample conductance with temperature. The titanium electrodes are connected to a conventional analog/digital converter device 30 and then to a computer or similar data processing device 32 for monitoring changes in conductance of the water in the chamber 24 over time. An ultraviolet lamp 34 is inserted through an orifice in the body portion 18, and this can be energized to supply ultraviolet light. The lamp 34 may be of the type known in the art as a low-pressure mercury vapor lamp. This class of lamp is chosen because its radiation is at primarily 253.7 nanometers wavelength with some 3% at 184 nanometers wavelength. Use of the 184 nanometer radiation, which is desired because light of this wavelength is very destructive to organic molecules, requires that the quartz window 20 be of a material which transmits this light well; a glass known as Supersil from Ameresil Co. works well. For similar reasons, the amount of water in the cell is deliberately kept small. The back of the chamber 38 formed in the body 18 may be mirrored as indicated at 36 to ensure high efficiency use of the ultraviolet light. The chamber 38 within which the lamp is located is desirably filled with dry nitrogen or other non absorbing gas. If it were filled with air or oxygen, for example, the oxygen would absorb some substantial fraction of the ultraviolet light emitted by the lamp 34.

Thus, in use, a sample of water from a process of interest is admitted to the chamber 24 and an initial background conductance reading is taken. The ultraviolet lamp is turned on, and the conductance of the water is monitored as a function of time by the computer 32. When the results of this monitoring indicate that the organic reaction has been completed, detected in a manner discussed in detail below, thus indicating that all the carbon in the organic matter has been converted to carbon dioxide, an output indicative of the total organic carbon content of the influent sample can be generated in accordance with the known relationship of carbon dioxide content in ultra-pure water to its conductance. See, e.g., *A New Approach to the Measurement of Organic Carbon*, Poirier et al. *American Laboratory*, December 1978, in which this relationship is shown. Note that in general, the water samples monitored contain sufficient oxygen that no additional oxidizers are required. If not, the use of oxidizing chemicals such as perchlorate should be avoided, as they are a source of additional impurities, in favor of pure oxygen.

The use of the single sample chamber 24 as shown in FIG. 1 has several advantages. Probably the primary among these is that no movement of water or carbon dioxide between an irradiation chamber and a conductance measurement chamber is required, as in the prior art Regan patent, thus greatly lessening the opportunity for impurities and contaminants to leach out from the instrument and associated support system into contact with the sample which would be required if such an approach were employed. Furthermore, the direct exposure of the electrodes 26 and 28 to the UV light emitted by the lamp 34 serves to keep them free of organic contaminants and the like. The net result is that generally the instrument itself is the only serious source of misleading ionic species in the water, "misleading" in the sense that it contributes spurious conductance not caused by oxidized carbon compounds. Accordingly, means must be found for compensation for these inaccuracies. This is particularly important in the case of low carbon level measurements, on the order of 100 ppb and less, because there the leaching of instrument materials such as the titanium of the electrode is sufficiently rapid that the conductance does not stabilize as a function of time, i.e., the titanium continually leaches at a rate such that the conductance appears to continually rise. Similarly, even if the instrument is made of a relatively inert material such as Teflon, this material can make a spurious contribution. A similar effect, though of different sign, can occur due to absorbtion of the carbon dioxide by the Teflon. Other instrument contributions are doubtless possible. In a manner subsequently described, the instrument system of the invention differentiates between all instrument contributions, which occur at a relatively constant rate during the period of the oxidation of the carbon, and the conductivity contribution of the carbon dioxide, at low-TOC concentrations. In such cases, the conductance value never stabilizes, because the instrument contribution continues. At higher organic concentrations, this is less of a problem, because there the instrument contributes relatively less to the total conductance of the water solution, and the conductance stabilizes to within experimental error to the asymptote of the conductivity curve due to oxidation of organics.

As mentioned, according to the invention of the present continuation-in-part application, the original cell design was substantially revamped to cope with certain problems and make certain improvements which were considered desirable. For example, it was found in experimentation with the original cell design that the Teflon material of the body of the cell had been absorbing and reemitting carbon dioxide which would, of course, lead to inaccurate TOC measurement. Further, it appeared possible that the Teflon degrades upon exposure to ultraviolet light. Hence, it was desired to eliminate all such materials and use only fused silica, titanium and Viton (trademark DuPont Corporation) in the cell construction. Further, it was deemed desirable to shield the Viton seals from direct UV radiation in case they should degrade thereupon.

Another object of the redesign of the cell was to lower its cell constant to approximately 0.1 in order to reduce electrical noise from the lamp.

Another difficulty with the initial cell design was that it did not have equal sensitivity throughout the sample. The new cell configuration is designed to ensure such equal sensitivity making the curve more ideal and predictable.

It was considered desirable to design the cell to maintain its integrity up to 400 psi, matching common pulsed loads. This is particularly desirable because while it would be possible to lower the water pressure, depressurization will typically cause bubbles to form which will interfere with accurate measurement. Also, providing the sample with the capacity to handle 400 psi means it can be used in substantially all laboratory process streams simply by closing a valve on its output side to trap a sample of water for test.

Another object of the new cell design was to provide for easy lamp replacement, easy assembly of the chamber and to simplify the machining required.

Another object of the cell re-design was to ensure that the electrode configuration would integrate any variations in temperature throughout the cell sample, thus ensuring further uniformity of results. For similar reasons, it was desired that the temperature sensor, critical to ensure correct compensation of the conductivity results, should be well isolated thermally from the environment while being in intimate contact with the solution, and that the bulk of the titanium metal, which forms the electrodes, should be isolated thermally from the environment so that the electrodes can quickly reach equilibrium with the sample temperature. Similarly, so that the temperature variation can be limited as much as possible, the amplifier used to amplify the signal should be thermally isolated from the chamber so that amplifier-generated heating is not transmitted to the sample.

Finally, it was necessary to design the chamber such that it is flushed quickly and thoroughly when a sample has been completely oxidized, so as to provide short purge time requirements, and to minimize any possibility of bubble entrapment or residual contamination.

Additional design goals which would be desirable though not as critical as those just discussed include making possible the addition of positive temperature control devices. For example, a thermoelectric cooler might be affixed to the sample housing and used in a feedback loop to control sample temperature, eliminating temperature compensation of conductivity as an essential part of the TOC determination.

It might also be desirable to provide two ultraviolet lamps in a chamber, possibly of different primary frequencies, to allow analysis for different organic compounds.

Finally, it was desirable to design the chamber to allow viewing of the sample chamber in situ, e.g. to determine that no foreign matter is present or the like.

Figure 11:
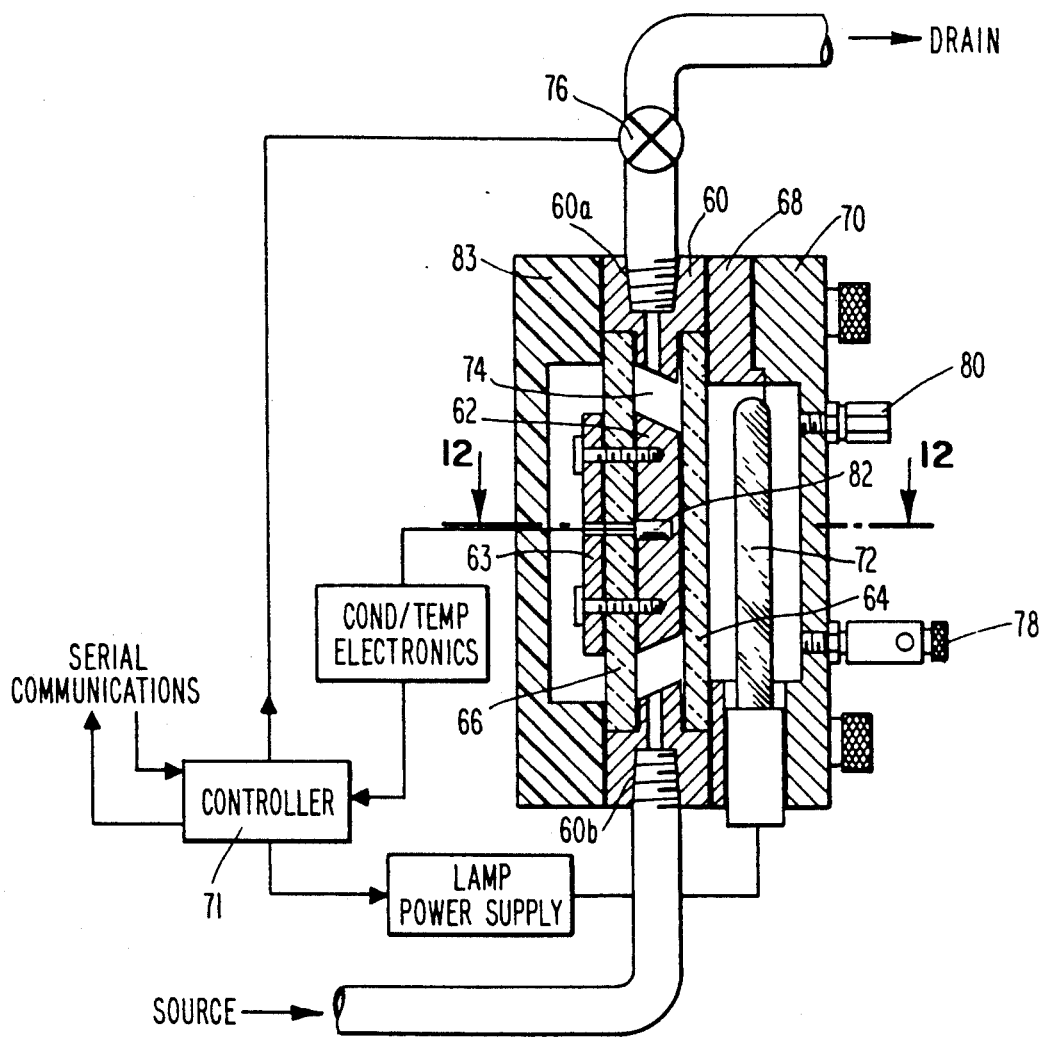
FIG. 11 shows a cross-sectional view of the later-preferred embodiment of the invention.
Figure 12:
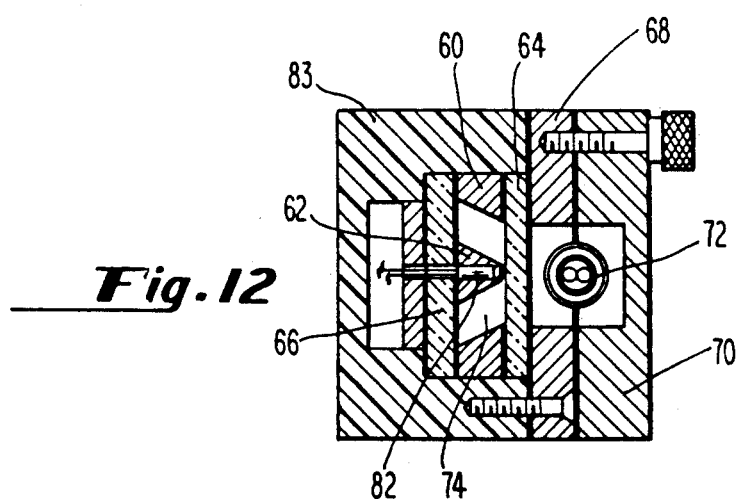
FIG. 12 is a cross section taken on the line 12—12 of FIG. 11.

FIGS. 11 and 12, which is a cross-sectional view taken along the line 12—12 of FIG. 11, show the presently preferred embodiment of the cell of the invention. FIG. 11 additionally shows its connections to the remainder of the system. Broadly, the water sample is admitted to a sample chamber defined by an outer electrode 60, an inner electrode 62 and glass windows 64 and 66. The outer electrode 60 is formed with an inlet port 60b and an outlet port 60a as shown. The inlet is plumbed directly to the pressurized ultrapure water source and the outlet is fed to a drain. A sample valve 76 is interposed in the outlet line. Under control of controller 71, the measurement cycle starts by closing the valve 76, halting the purge flow and trapping a sample of water to be analyzed. The background temperature-corrected conductivity between electrodes 60 and 62 is measured. An ultraviolet lamp 72 is turned on and oxidizes the organic material present in the sample. The resultant temperature-corrected change in conductivity is measured, the $CO_2$ concentration calculated therefrom and the organic concentration displayed as parts per billion total organic carbon on a display on controller 71. The valve 76 is then opened, allowing a new supply of water to purge the chamber and clean it for the next cycle.

The sample chamber is constructed entirely of titanium and high-purity synthetic fused silica, such as that referred to as Supersil, mentioned above. The seals required to contain the sample are formed of a durable material such as Viton, and are shaded from direct ultraviolet exposure, in order to avoid degradation and consequent interference with the measurement. Preferably, the sample chamber is vertically oriented with the outlet on top to allow easy flushing of bubbles. The chamber is designed to operate at system pressure with a continuous pressure rating of 150 psi and a pulse rating of 400 psi. Because the sample valve 76 is a potentially severe source of contamination in low concentration TOC measurement, it has been located downstream from the sample, eliminating these problems.

As discussed earlier, use of 184 nanometer radiation is highly desirable because this breaks up molecular oxygen to provide radicals for combination with the carbon, and is a very powerful oxidant. However, the low-pressure mercury vapor lamp used outputs only some 3-6% 184 nm UV. The remainder is primarily 254 nanometer UV radiation. Accordingly, it is important that the glass selected transmit both frequencies very well, and the Supersil material mentioned above does so. It will be recognized by those skilled in the art that the absorbtivity of the 184 nanometer radiation by oxygen means that it would be undesirable to have the lamp 72 surrounded by air. A fill valve 78 and a check valve 80 are provided for filling a sealed chamber enclosing the lamp 72 with nitrogen. Ordinarily, of course, this chamber would be filled with nitrogen at the factory but in the event lamp replacement is required, this allows simple purging by the user.

As will be appreciated from the view of FIG. 11, the conductivity sensor is in fact integral to the sample chamber. The opposing electrodes 60 and 62 are equidistant to produce equal volume sensitivity throughout and are spaced to provide a cell constant just over 0.1. The surfaces of the electrodes are constantly exposed to intense short wave ultraviolet radiation, which keeps them clean and free of organic contaminents which would interfere with high accuracy conductivity measurements. Contained within the center electrode 62 is a solid-state temperature sensor 82, typically a Model AD 590LF from the Analog Devices Company. Thermistors could also be used. This sensor is capable of temperature measurement accuracy of ±0.05° C. The large surface area and large electrode volumes serve to integrate the sample temperature over the entire chamber thereby providing an accurate representation of the mean temperature of the sample. The center electrode 62 is clamped to the glass window 66 by way of a backplate 63, which confines the temperature sensor 82 in position.

The cell assembly is completed by a transparent plastic rear cover 83. Through it one can observe the UV light from the lamp passing through both the first and second windows 64 and 66, around the inner electrode. The leads to the temperature sensor 82 and the center electrode 62 pass through a hole in the rear cover 83, while electrical connection to the outer electrode can be made directly thereto. It will be observed that the lamp 72 is clamped between members 68 and 70, formed of aluminum, and can be removed without breaking of the seals of the sample chamber, enabling inspection of the chamber in situ.

Figure 13:
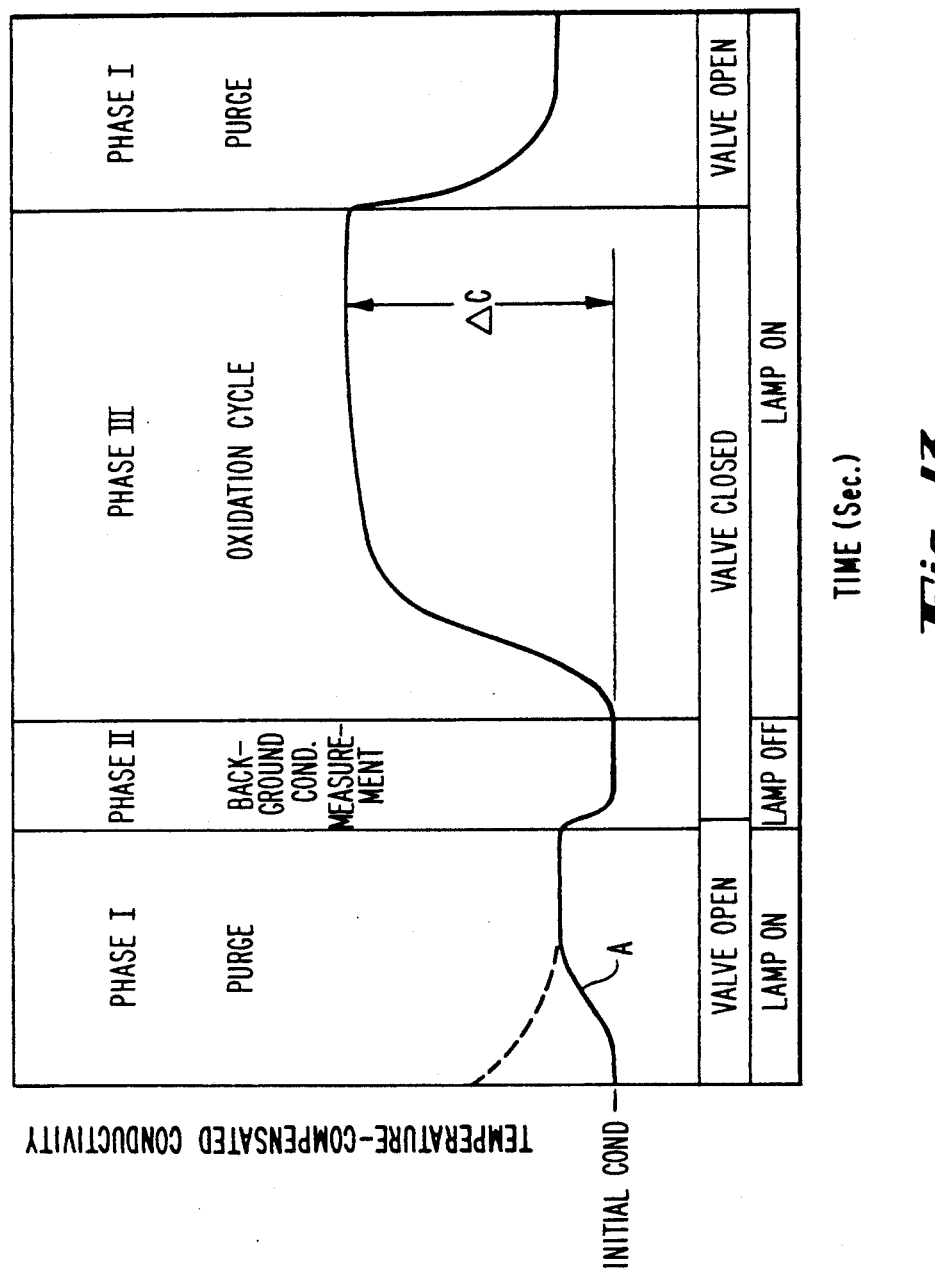
FIG. 13 is a timing chart, with a plot of typical conductivity data.

FIG. 13 shows the sequence of operation of the instrument according to the invention. The graphed data shown at A represents conductivity measured as a function of time. The two bar graphs along the bottom of FIG. 13 show the sequence of opening and closing of the valve 76 and the periods during which the lamp 72 is illuminated. Thus, in phase I the valve is opened and the lamp 72 is turned on. During this period, water from the source is passed through the sample chamber continuously, providing a purge effect. The light is on to oxidize any material which may remain in the chamber. The lamp is turned off leaving the valve open for a short time to allow purging of any residual $CO_2$. The valve is then closed for Phase II during which period the background conductivity, that is, the conductivity of the sample before oxidation, is measured, compensated for temperature. The valve stays closed in Phase III but the lamp is turned on. During this time, the oxidation of organics to $CO_2$ causes the conductivity to gradually rise, typically to an asymptotic value as shown, which behavior is discussed more fully hereafter. The difference from the initial and final conductivity $\Delta C$ is shown. When properly temperature compensated, $\Delta C$ provides an indication of the total organic carbon content of the initial water sample. Phase I is then begun again as shown at the right side of FIG. 13.

The following discussion of FIGS. 2 through 10 appeared in substantially identical form in the parent application and remains here because the analysis provided is applicable in many cases. Following this discussion, additional material explaining new understanding of the oxidation process and referring to FIGS. 14–17 will be provided.

Figure 2:
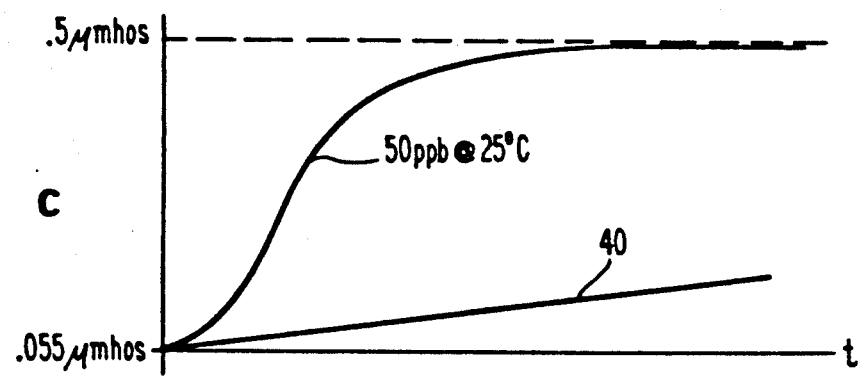
FIGS. 2 through 9 show various curves useful in understanding the operation of the system of the invention.

FIG. 2 shows an idealized plot of the conductivity of water corrected for temperature and instrument background variations, the organic carbon content of which is being oxidized by ultraviolet light, versus time. Here the vertical axis is conductivity C, which can vary from the conductivity of pure water, 0.055 micromhos at 25° C. at the origin to on the order of 0.5 micromhos for 50 ppb organic-carbon contaminated water through perhaps 5 micromhos at water contaminated at 5 ppm, both again at 25° C. It will be observed that the exemplary curve shown approaches an asymptotic limit, which is usual. Typically, this limit will be approached in on the order of one to five minutes after commencement of exposure of the water to ultraviolet light. It will also be observed that the curve is substantially non-linear.

Figure 3:
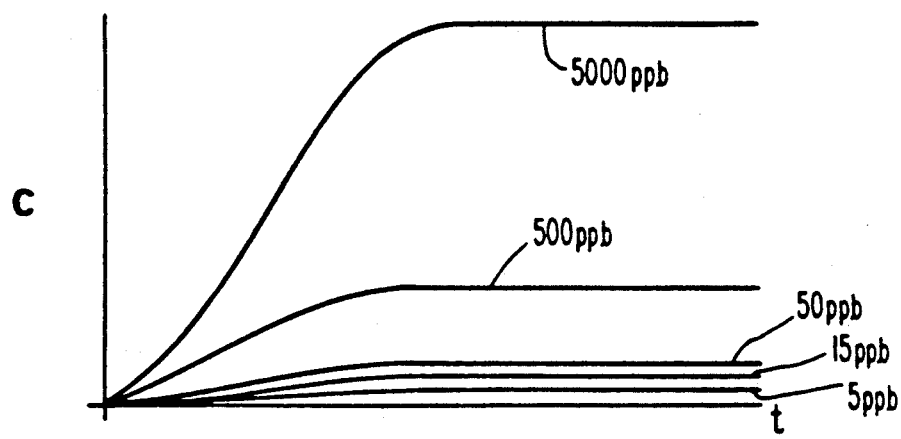

FIG. 3 shows a number of additional curves of the conductivity of water samples containing various amounts of organic carbon, as noted, being oxidized as a result of exposure to ultraviolet radiation as a function of time. It will be observed that the relative differences between the asymptotic portions of the curves for widely varying concentrations of contaminants are not very great, particularly in the higher-TOC region. That is, the ultimate conductivity of water samples after oxidation of relatively widely varying amounts of organic material are quite similar. Accordingly, if these samples are to be distinguished from one another by measurement of conductivity, any background noise or other spurious contribution must be rigorously eliminated, and the present invention is designed to achieve this goal.

Figure 4:
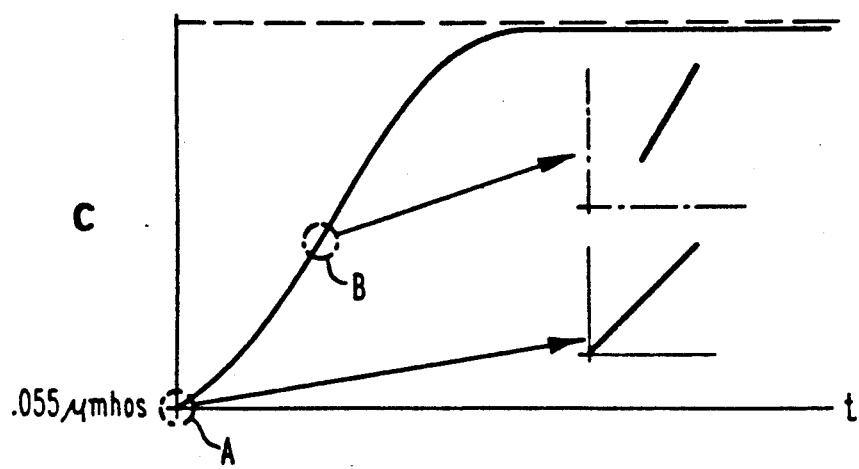

FIG. 4 shows a curve of the temperature-corrected conductivity of organic free water sealed in the sample chamber and irradiated with ultraviolet light as a function of time, varying due to leaching of titanium into the water, or other instrument contribution. Here the time scale is on the order of several days. It will be observed that this curve also approaches an asymptotic limit as the water becomes saturated by the instrument contribution but that the portion of the curve of interest, that within a circle A of a few minutes' radius around the origin, as shown enlarged on the right side of FIG. 4, is relatively linear. As indicated at B, other small portions of the total curve are also substantially linear. Again, the origin is at 0.055 micromhos, the conductivity of pure water, and the conductivity can rise to a very high value in the case of saturated water. However, the time required for approaching the saturation point is on the order of days.

If one expands the very leftmost portion of the curve of FIG. 4, indicating variation of conductivity due to the instrument contribution and inserts this at 40 into FIG. 2, showing variation in conductivity due to oxidation of organic material to carbon dioxide, and sums the two curves, thus providing a curve indicative of the typical shape of real data detected in measurements made according to the invention, the horizontal portion of the curve of FIG. 2 will be replaced instead with a linear portion superimposed upon the non-linear portion of the curve of FIG. 2, and this is what is frequently observed.

Figure 5:
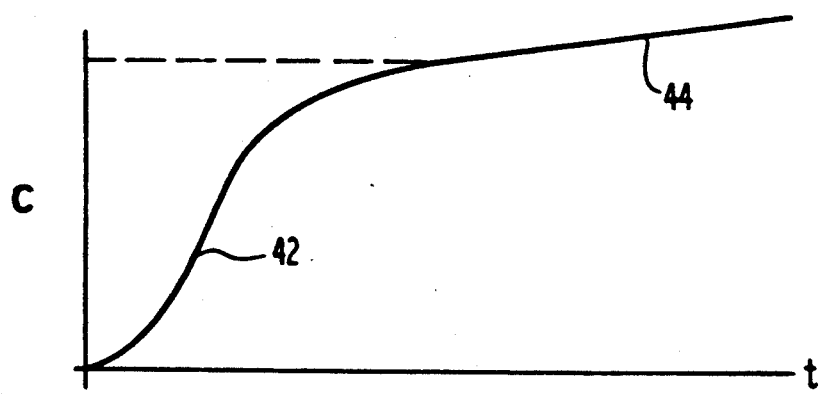

FIG. 5 shows an example of typical test data of this kind. The non-linear portion 42 of the curve is similar to that of FIG. 2, whereas the linear but non-horizontal portion 44 is the result of the addition of the linear portion of curve 40 of FIG. 2 due to instrument background.

Figure 6:
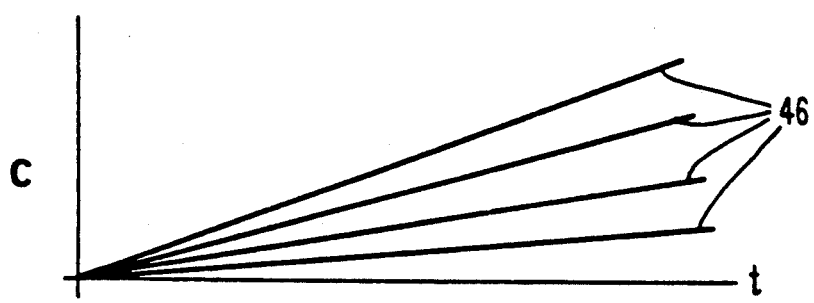

It might be considered, therefore, to be a simple matter to measure the curve of saturation of a typical instrument design, curve 40 of FIG. 2, e.g., at initial manufacture of the instrument, and subtract this from actual test data so as to yield a compensated curve. However, in fact this does not yield accurate results. FIG. 6 shows one reason why. The several curves 46 shown there all correspond to the curve 40 in FIG. 2 and indicate that while the instrument contribution may be relatively linear for the several minutes during which a given TOC measurement is made, this rate is not the same for all samples and under all circumstances, so that these measurements are not repeatable, preventing a base line measurement from being established for correcting test data as suggested. Furthermore, it appears likely to the applicants that exposure of the instrument material to ultraviolet light may also increase its contribution is a not entirely predictable fashion, such that this effect would similarly lead to inaccuracies if simple subtraction of a baseline correction were made to actual experimental data. Accordingly, more sophisticated techniques for determining when the organic carbon oxidation reaction is complete and for calculating the correction to be applied are required, and these are provided by the invention as well.

Figure 7:
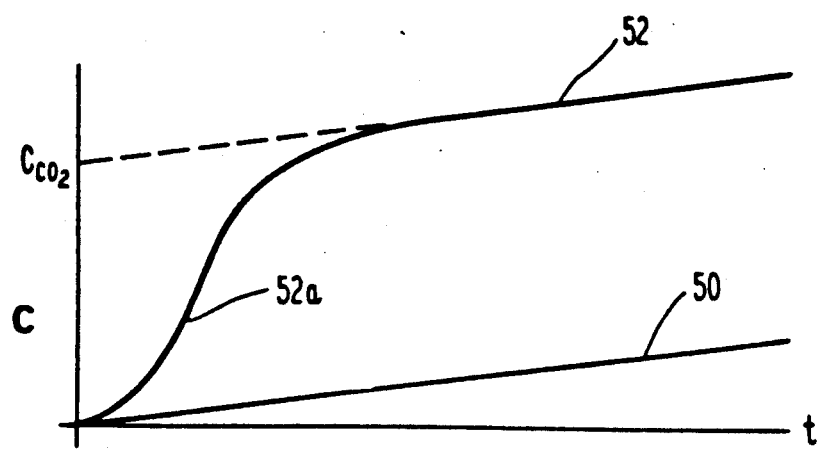

FIG. 7 shows an enlarged view of a curve comparable to that shown in FIG. 5, illustrating the differentiation between the instrument conductivity contribution versus time curve 50, which is substantially linear for the short time (e.g. 1–10 minutes) shown and the curve 52, which plots measured conductivity versus time data. The non-linear portion 52a of curve 52 is that due to oxidation of carbon components to form carbon dioxide. Once this reaction is essentially complete, curve 52 also becomes linear. The subsequent increase in temperature-corrected conductivity is due solely to the instrument contribution. Therefore, the linear portion of curve 52 can be extended leftward to the conductivity axis, where the intercept $^{C}CO_2$ provides a measure of the difference in conductivity between the total curve 52 and the portion 50 contributed by the instrument, i.e., a measure of the portion contributed solely by the carbon dioxide resulting from oxidation of organic carbon. This value for conductivity $^{C}CO_2$ can then be directly converted to a value for total organic carbon in the sample, e.g., using the data shown in the article by Poirier et al referred to above.

Figure 8:
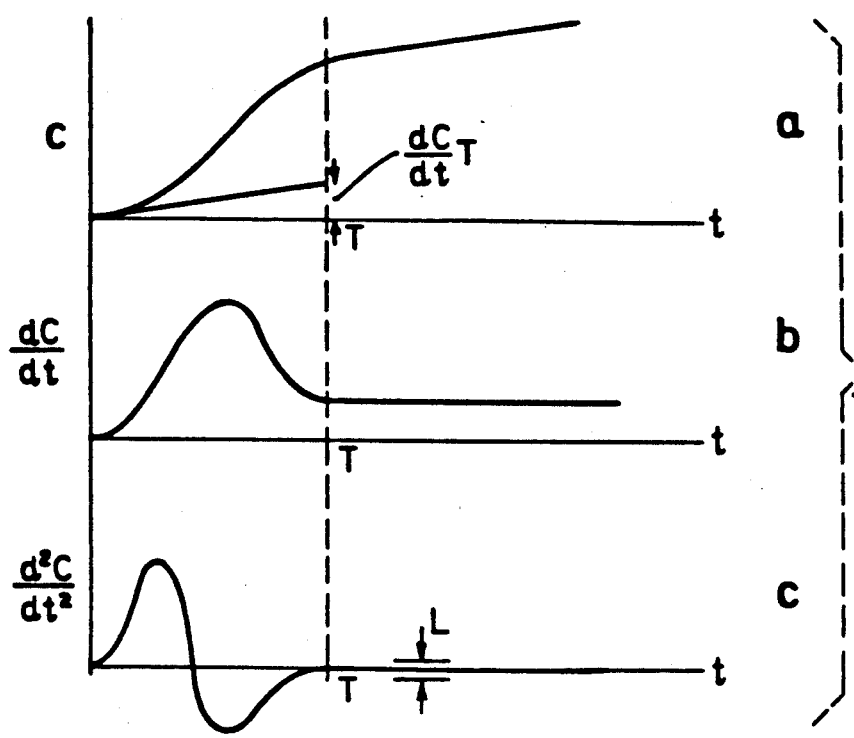

The sole difficulty with the approach just outlined is that it is not necessarily easy to determine by computer when the curve 52 has become linear. FIG. 8 shows three curves, denoted FIGS. 8a through c, which illustrate a way in which this determination can be made. FIG. 8a is a reproduction of curve 52 of FIG. 7, showing the characteristic non-linear/linear shape of the conductance versus time curve. FIG. 8b shows the time derivative of this curve, denominated dC/dt on the vertical axis, versus time. It will be observed that the first derivative essentially reaches a horizontal but non-zero value when the reaction is completed, indicated by the dashed line at time T. FIG. 8c shows the second time derivative of conductivity plotted versus time, $d2C/dt2$. When the value of of the second derivative settles to within some small specified value L of zero, designed to account for sampling errors and the like, the conductivity curve of FIG. 8a has become linear, indicating that oxidation is complete. Assuming all values are appropriately temperature-compensated, one can then generate a value for the correction to be applied simply by subtracting the contribution given by the instrument, dC/dt T, the slope of the instrument contribution curve, dC/dt, times T, the time at which oxidation is determined to be complete, from the total change in conductivity at time T; the remainder is equal to the conductivity contribution of the carbon dioxide, which, as mentioned above, can be directly converted to a value for total organic carbon in the water sample prior to oxidation by the UV light.

Figure 9:
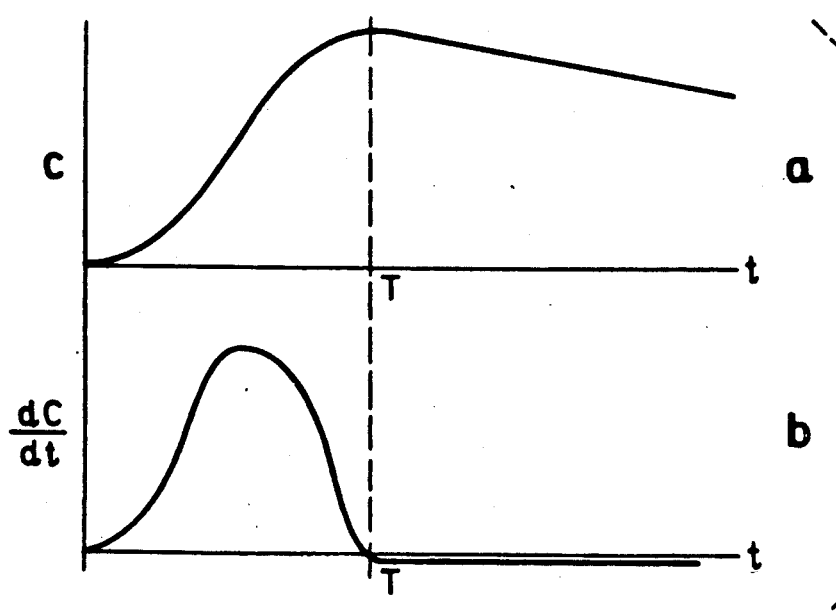
Figure 10:
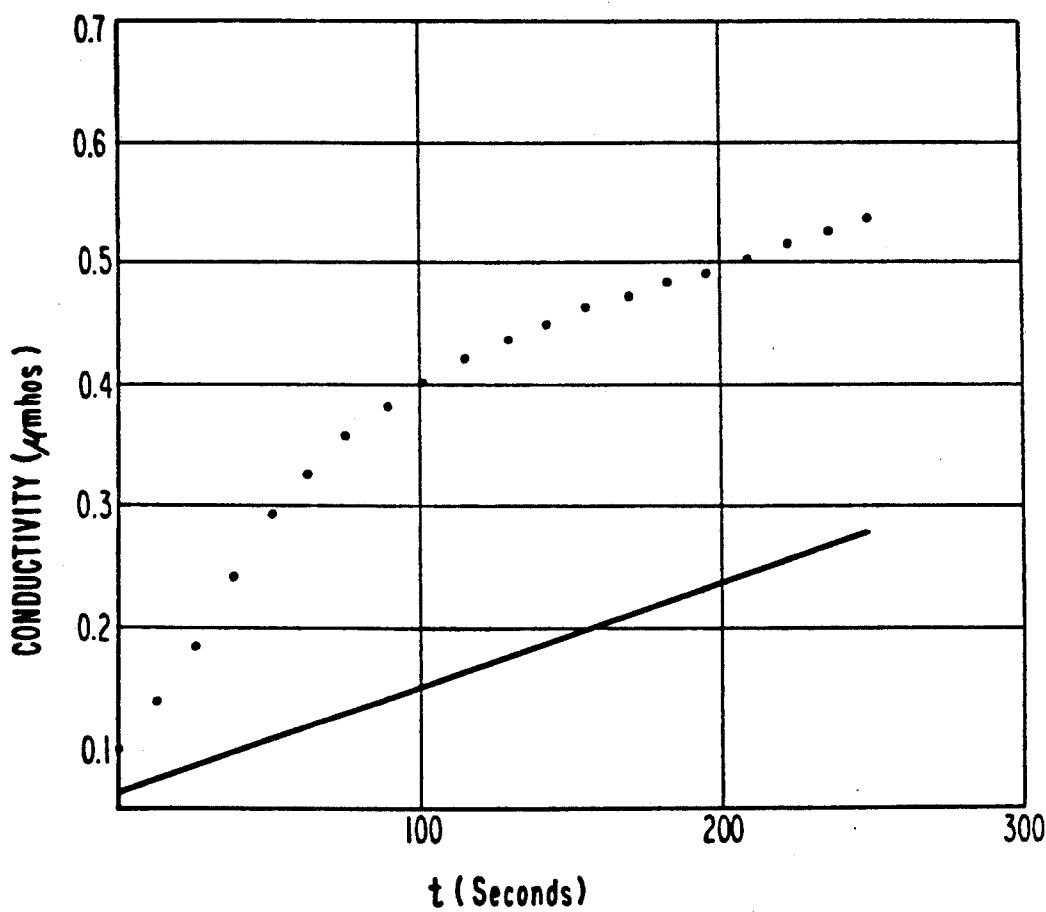
FIG. 10 shows an example of actual test data.

The situation just described and the curves shown in FIG. 8 occur where the contribution to the conductivity of the water of total organic carbon is relatively low compared to that caused by the instrument. In such situations, use of the second derivative approaching zero to indicate completion of oxidation approach should be used. In other cases, where the total organic carbon content is relatively high, or when the instrument is first installed, differing approaches are indicated. FIG. 9 shows such a situation, in which the conductivity of the water, shown in FIG. 9a, reaches a peak and then begins to decline. This occurs, for example, because, for example, the carbon dioxide diffuses through the water lines connected to the sample cell, reducing the conductivity of the water. It is clear, however, that once the conductivity has peaked and begun to decline, the reaction has been completed. Accordingly, the conductivity data at this point indicates the total organic carbon content of the sample. This value can be noted readily by monitoring the time derivative of this curve, shown in FIG. 9b. When the derivative reaches zero or becomes negative, as shown, the reaction has been completed, and the conductivity at this time indicates that the amount of total organic carbon being oxidized to carbon dioxide can be calculated. Here, the contribution from the instrument is minor and can be ignored.

The applicants find that with a sample cell substantially as shown, if one simply monitors both first and second time derivatives, either the first derivative or the second derivative will approach zero, as in FIGS. 9 and 8, respectively, depending on the total organic content. The FIG. 8 curve is usually seen at TOC values less than 50 ppb, while the FIG. 9 curve becomes typical at higher TOC concentrations, the threshold being a function of actual instrument background contribution.

Those skilled in the art will recognize that there are several ways in which the first and second time derivatives as described in FIGS. 8 and 9 can be calculated and evaluated. It is envisioned that in the ultimate embodiment, dedicated analog differentiator devices could be used. Possibly these could be integrated with other circuit elements designed to indicate the total organic carbon directly. In the meantime, it will be sufficient teaching to those skilled in the art to note that a general purpose digital computer together with a conventional analog-to-digital converter device for conversion of conductivity data into digital values can be used.

In a preferred embodiment which has been successfully tested, the conductivity is measured every 13 seconds, and the last 5 data points thus generated are successively curve-fit to a straight line the slope of which is monitored to determine whether the first derivative has approached the horizontal. The second derivative is generated similarly by curve-fitting five successive first derivative values to a straight line the slope of which is similarly measured. Whichever derivative first approximates zero is then used as described above in derivation of the conductivity contributed by oxidation of total organic carbon. The approach selected is thus dependent on the relative amount of total organic carbon as compared with the rate at which the instrument contributes to the conductivity of the water sample.

The following Example I is a reproduction of the output of an actual run in which the total organic content of a water sample was measured as described above. The six columns of data represent, reading left to right, sampling time, elapsed time, conductivity in micromhos, sample temperature in °C. (measured as the rear of the center electrode) and the first and second time derivatives of the conductivity measurements. The last two items mentioned do not begin until the fifth and ninth entries, due to the five-sample curve-fitting technique used, and because the first derivative is used in calculation of the second derivative. The conductivity measurements shown are graphed in the upper curve of FIG. 10. As can be observed, the curve is linear at its rightmost extremity indicating that the oxidation reaction is complete, and that further changes in conductivity are due to instrument contribution at the linear rate shown by the lower curve.

organic matter to ultraviolet light were discussed. FIG. 9 discussed the case in which the conductivity value either reaches a constant or went into a steady decline after a period of time. This will be referred to hereinafter as a Case I contaminant. Note that the loss of $CO_2$ causing a steady decline in the measured conductivity with time can be substantially eliminated by proper instrument design. FIG. 8 displayed the case in which the conductivity varied nonlinearly for a period of time and then reached a linear, gradually increasing condition. This will be referred to hereinafter as a Case II condition. It has since been discovered that there is a third type of contaminant which reaches an intermedi-

EXAMPLE I

| Time (HR:MIN:SEC) | Elapsed Time (SEC) | Conductivity (MICROS) | Temp. (°C.) | DC/DT (MICROS) /SEC | D2C/DT2 (MICROS) /SEC2 |
|---|---|---|---|---|---|
| BACKGROUND MEASUREMENT | | | | | |
| 9:38:35 | 0 | .065 | 23.81 | 0 | 0 |
| LAMP ON, OXIDATION BEGINS | | | | | |
| 9:38:50 | 0 | .099 | 24.02 | 0 | 0 |
| 9:39:3 | 13 | .139 | 24.16 | 0 | 0 |
| 9:39:16 | 26 | .185 | 24.32 | 0 | 0 |
| 9:39:28 | 38 | .243 | 24.49 | 0 | 0 |
| 9:39:41 | 51 | .293 | 24.67 | 3.8874803E−03 | 0 |
| 9:39:54 | 64 | .326 | 24.86 | 3.8090918E−03 | 0 |
| 9:40:6 | 76 | .357 | 25.05 | 3.3872851E−03 | 0 |
| 9:40:19 | 89 | .381 | 25.25 | 2.6544229E−03 | 0 |
| 9:40:32 | 102 | .401 | 25.42 | 2.1485315E−03 | −3.5957636E−05 |
| 9:40:45 | 115 | .42 | 25.57 | 1.8229599E−03 | −4.0926163E−05 |
| 9:40:59 | 129 | .436 | 25.73 | 1.4988779E−03 | −3.526866E−05 |
| 9:41:12 | 142 | .448 | 25.9 | 1.278984E−03 | −2.5812067E−05 |
| 9:41:25 | 155 | .462 | 26.08 | 1.1222675E−03 | −1.9353856E−05 |
| 9:41:39 | 169 | .47 | 26.21 | 9.398618E−04 | −1.6001923E−05 |
| 9:41:52 | 182 | .483 | 26.32 | 8.734737E−04 | −1.2081323E−05 |
| 9:42:6 | 196 | .491 | 26.47 | 7.912241E−04 | −9.05495E−06 |
| 9:42:19 | 209 | .502 | 26.58 | 7.4734534E−04 | −6.680404E−06 |
| 9:42:32 | 222 | .514 | 26.68 | 8.0459425E−04 | −2.872771E−06 |
| 9:42:46 | 236 | .525 | 26.83 | 7.978849E−04 | −1.039593E−06 |
| 9:42:59 | 249 | .534 | 26.96 | 8.219301E−04 | 8.10708E−07 |
| OXIDATION COMPLETE | | | | | |

Elapsed Time (Oxidation) = 4 minutes, 9 seconds
Initial Background Conductivity = .065 micromhos/cm
Final Background Conductivity = .279857 micromhos/cm
Temperature change = 3.15 degrees C.
Delta Conductivity (Instrument) = .20466059 Micromhos/cm
Delta Conductivity ($CO_2$) = .254143 micromhos/cm
TOC = 10.341327 PPB
Uncorrected TOC = 33.676432 PPB The computer output reproduced above indicates that the oxidation reaction proceeded to completion in some 4 minutes, 9 seconds, that the initial background conductivity of the water was 0.065 micromhos/cm, that it rose due to instrument contribution to a final value of 0.279 micromhos/cm and that the temperature change (used by the computer to correct the conductivity values so as to be comparable to one another) was 3.15° C. The value for L used was $\pm 10^{-5}$; after five successive values of the second derivative of the conductivity value were less than L, the change in conductivity due to the instrument was calculated to be some 0.204 micromhos/cm, and that due to oxidation of carbon was 0.254 micromhos/cm. From this last figure an initial total organic content of the water sample of some 10.3 parts per billion was calculated; if the correction for the instrument contribution had not been applied, the apparent TOC value would have been 33.6 ppb. The method of the invention of correction for this source of spurious conductivity is thus clearly beneficial.

It will be recalled from the discussion of FIGS. 8 and 9 that essentially two cases of conductivity variation with time upon exposure of a water sample containing ate peak and then declines to a steady value. This will be referred hereinafter as a Case III contaminant. Case III behavior is believed to be encountered when the contaminant is oxidized through intermediate products which are of higher conductivity than the final $CO_2$ product. Acetone provides a good example of this behavior. Another common chemical which is oxidized through intermediates is butanol.

Figure 14A:
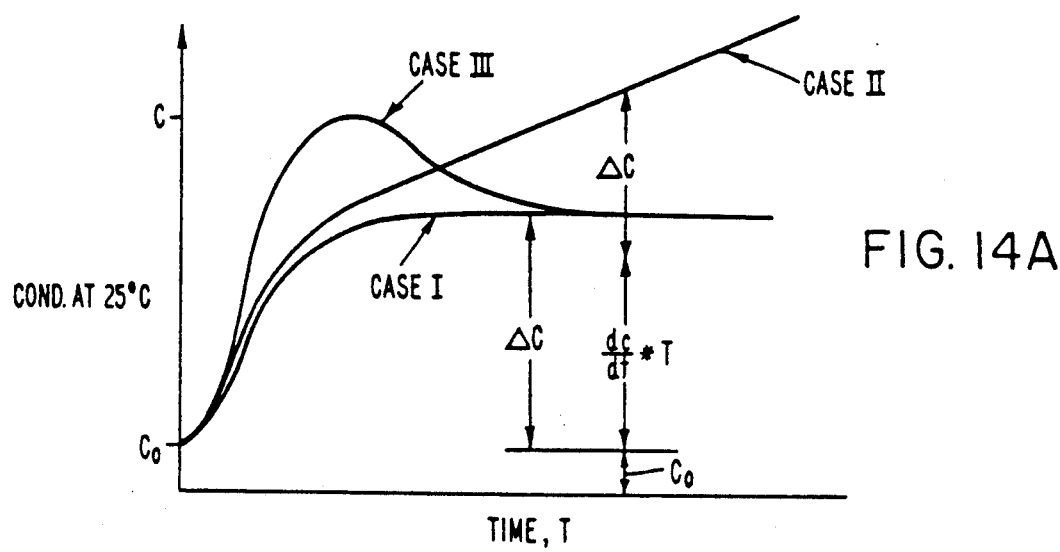
FIG. 14 is a graph of idealized conductivity data, and the first and second time derivatives thereof.
Figure 14B:
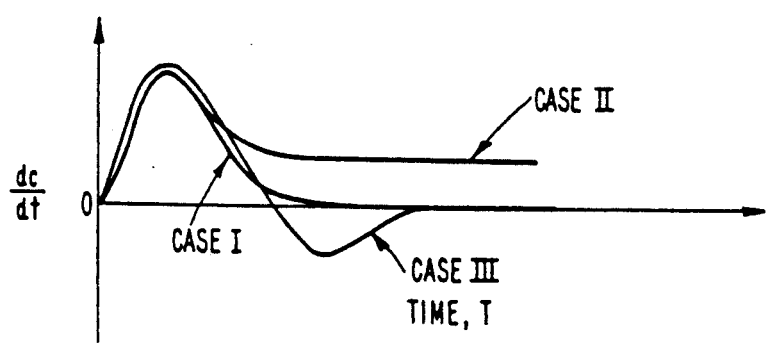
Figure 14C:
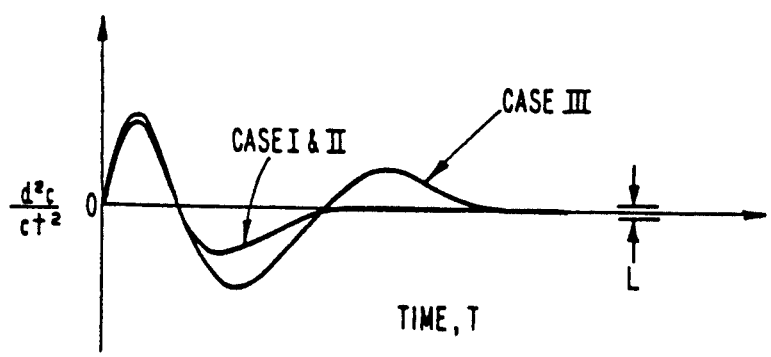

A comparison of idealized examples of Cases I, II and III behavior is shown in FIG. 14. FIG. 14(a) shows conductivity as a function of time, for Cases I, II and III. FIG. 14(b) shows the first time derivative of the conductivity curves, and the curves of FIG. 14(c) show the second time derivative of conductivity of all three cases. As shown and described above, the Case I behavior corresponds generally to that shown in FIG. 9 ending at a linear asymptote (either horizontal or dropping) while the Case II behavior (a rising asymptotic limit) is that shown in FIG. 8. The Case III data as shown in FIG. 14(a) exhibits conductivity reaching a peak at some early value and then declining to a final asymptotic value after the oxidation reaction is complete. It is a relatively straightforward matter to determine when a Case III contaminant has been completely oxidized, i.e. when its conductivity becomes a constant, by monitoring the first and second derivatives as discussed above in connection with Type Case I and II behavior. A further improvement can be made by noting that the point at which the second time derivative of the Case III conductivity, FIG. 14(c), passes through zero for the second time, is the inflection point of the conductivity verses time plot of FIG. 14(a) and that in neither Case I nor Case II do the second derivatives pass through zero twice. Accordingly, when the second time derivative passes through zero a second time, it can be concluded that the sample includes a Case III containment. When the first time derivative thereafter approaches zero, the conductivity is reaching its asymptotic limit at which time compensation can be made for the background conductivity of the sample, $C_O$ in FIG. 14(a) which is then subtracted from the total change in conductivity, $\Delta C$, which is then temperature-corrected to yield an accurate conductivity value which can then be converted to a TOC value as discussed above.

Accordingly, analysis of the Type III data is accomplished by a refinement of the techniques used in connection with data from Cases I and II. The second derivative is monitored to determine whether it goes negative, then passes through zero again. If the first derivative is negative when the second derivative curve reaches zero for the second time, a Case III curve is in progress, and the reaction has proceeded to the inflection point of the corresponding conductivity curve. Two different tests can now be applied to determine whether a Case III curve has approached its asymptotic limit: either the first derivative can be monitored to determine when it is at an acceptably low level, or the second derivative of the conductivity can be monitored until it again approaches zero from the positive side.

Data shown hereinafter indicates that in many cases Type III reactions are not completed for a relatively long period of time, typically 15 or 20 minutes. It is recognized that as the last portion of the curve approaches as asymptotic limit, presumably it would be possible to curve fit an exponential or similarly-shaped curve to this portion of the data and calculate the value of the asymptote from this. However, as yet no entirely satisfactory equation has been developed. It does appear that the peak value reached by the conductivity is as repeatable as the final value reached by the conductivity. Accordingly, if one monitors a series of peak conductivity values obtained from samples from the same laboratory equipment, process plant, testing station or the like, and finds that the peak values reached by the conductivity are all within a predetermined limit, e.g. $\pm 2\%$, of one another, one can conclude that the final conductivity value will similarly be within $\pm 2\%$ of that of a run continued for the full period, and can presume that accordingly there has been no significant change in the organic concentration of the water sample tested. This is very useful in continuous monitoring of a given process, and can readily be adapted to trend detection and display. In practice, the controller 71 operating the system monitors conductivity of a succession of samples, dumping them immediately after reading the peak value, except when the peak value departs by more than a predetermined value from one or more previous peak values.

The following Example II gives an indication of the data which is generated during an extended analysis of a sample containing a Type III organic contaminant. As can be seen, the example is generally comparable to that shown above as Example I through additional data columns are presented. It should be emphasized that the data given for the first and second time derivatives necessarily do not show values corresponding to the first few conductivity values, due to the nature of the process used to derive these functions, which is as discussed above. It will be observed that after the run had proceeded for 208 seconds, it was made clear that it was a Case III contaminant. This was determined by noting that the first derivative had become negative. When the second derivative of the conductivity became positive after 317 seconds (for the second time, in fact, although the first positive values do not appear in Example II), the peak value of the conductivity was compared to an earlier run and it was determined that the deviation was some 0.843%. This was greater than the deviation allowance of 0.5%, and accordingly an extended run was undergone. Finally, after some 1087 seconds, oxidation was deemed complete. The total organic carbon reading was given as 129.7 parts per billion.

EXAMPLE II

| TIME (SECONDS) | TEMPERATURE (DEGREES C.) | DELTA COND @ 25° C. (MMHOS/CM) | DC/DT 1E-5 (MMHOS/DM/SEC) | D2C/DT2 1E-5 (MMHOS/CM/SEC2) | REAL-TIME TOC (PPB) | RAW COND (MMHOS/CM) |
|---|---|---|---|---|---|---|
| 4 | 28.664 | 0 | 0 | 0 | 0 | .0825 |
| 16 | 29.103 | .05908 | 0 | 0 | 2.404 | .1474 |
| 28 | 29.421 | .24178 | 0 | 0 | 17.5 | .3478 |
| 40 | 29.738 | .45866 | 0 | 0 | 50.45 | .5888 |
| 52 | 30.047 | .63815 | 1396.1 | −6.7388 | 90.06 | .7913 |
| 64 | 30.334 | .78639 | 1171.6 | −13.006 | 131.2 | .9611 |
| 76 | 30.598 | .91193 | 1006 | −12.342 | 172 | 1.1063 |
| 88 | 30.838 | 1.021 | 890.95 | −9.335 | 211.9 | 1.2342 |
| 100 | 31.056 | 1.121 | 803.74 | −7.8472 | 252.1 | 1.3523 |
| 112 | 31.253 | 1.2141 | 723.54 | −7.7782 | 292.6 | 1.4629 |
| 124 | 31.435 | 1.2977 | 629.36 | −8.4882 | 331.6 | 1.563 |
| 136 | 31.602 | 1.3683 | 517.6 | −9.2891 | 366.4 | 1.6485 |
| 148 | 31.757 | 1.4231 | 396.31 | −9.501 | 394.6 | 1.716 |
| 160 | 31.899 | 1.4625 | 277.67 | −8.9755 | 415.5 | 1.7657 |
| 172 | 32.033 | 1.488 | 173.31 | −7.8684 | 429.3 | 1.7993 |
| 184 | 32.16 | 1.5016 | 86.776 | −6.4571 | 436.8 | 1.8195 |
| 196 | 32.279 | 1.5063 | 18.624 | −5.0622 | 439.4 | 1.8289 |
| 208 | 32.391 | 1.5042 | −32.277 | −3.8177 | 438.2 | 1.8303 |
| ## TOC CASE #3 ANALYSIS BEGINS ## | | | | | | |
| 220 | 32.498 | 1.4969 | −69.678 | −2.8059 | 434.2 | 1.8255 |
| 232 | 32.601 | 1.4861 | −96.476 | −2.038 | 428.3 | 1.8166 |
| 244 | 32.699 | 1.4729 | −116.06 | −1.4334 | 421.1 | 1.8046 |

EXAMPLE II-continued

| TIME (SECONDS) | TEMPERATURE (DEGREES C.) | DELTA COND @ 25° C. (MMHOS/CM) | DC/DT 1E-5 (MMHOS/DM/SEC) | D2C/DT2 1E-5 (MMHOS/CM/SEC2) | REAL-TIME TOC (PPB) | RAW COND (MMHOS/CM) |
|---|---|---|---|---|---|---|
| 256 | 32.794 | 1.4578 | −130.1 | −1.0296 | 413 | 1.7903 |
| 269 | 32.892 | 1.44 | −139.92 | −.72141 | 403.5 | 1.7728 |
| 281 | 32.979 | 1.4224 | −146.93 | −.46426 | 394.2 | 1.755 |
| 293 | 33.063 | 1.4043 | −151.41 | −.26591 | 384.8 | 1.7368 |
| 305 | 33.144 | 1.3859 | −152.85 | −.099304 | 375.3 | 1.7177 |
| 317 | 33.223 | 1.3673 | −152.68 | .033286 | 365.9 | 1.6986 |
| 329 | 33.3 | 1.349 | −151.69 | .086197 | 356.7 | 1.6795 |
| 341 | 33.374 | 1.331 | −149.81 | .11268 | 347.8 | 1.6606 |
| 353 | 33.446 | 1.313 | −148.71 | .10928 | 339 | 1.6417 |
| 365 | 33.516 | 1.2954 | −147.27 | .094006 | 330.5 | 1.623 |
| | | DEVIATION = .84375617% | | | | |
| | | EXTENDED OXIDATION IN PROGRESS | | | | |
| 379 | 33.595 | 1.2746 | −146.23 | .10703 | 320.6 | 1.6011 |
| 391 | 33.662 | 1.2574 | −145.11 | .10531 | 312.5 | 1.5825 |
| 403 | 33.726 | 1.2399 | −143.36 | .14621 | 304.4 | 1.5638 |
| 415 | 33.789 | 1.2229 | −142.01 | .1637 | 296.6 | 1.5455 |
| 427 | 33.85 | 1.2058 | −139.21 | .16905 | 288.9 | 1.5271 |
| 439 | 33.91 | 1.1892 | −137.25 | .18477 | 281.5 | 1.5091 |
| 451 | 33.97 | 1.1731 | −135.25 | .15184 | 274.4 | 1.4915 |
| 463 | 34.027 | 1.157 | −133.14 | .14777 | 267.4 | 1.474 |
| 475 | 34.084 | 1.1409 | −131.92 | .15438 | 260.5 | 1.4566 |
| 487 | 34.139 | 1.1253 | −130.16 | .16125 | 253.9 | 1.4393 |
| 499 | 34.193 | 1.1098 | −127.84 | .18818 | 247.4 | 1.4223 |
| 511 | 34.246 | 1.0945 | −125.4 | .22807 | 241.1 | 1.4054 |
| 523 | 34.299 | 1.0796 | −122.89 | .25882 | 235 | 1.389 |
| 535 | 34.351 | 1.0651 | −119.21 | .26757 | 229.2 | 1.373 |
| 547 | 34.401 | 1.508 | −115.41 | .31109 | 223.5 | 1.3574 |
| 559 | 34.45 | 1.0373 | −112.55 | .29948 | 218.2 | 1.3423 |
| 571 | 34.498 | 1.0242 | −107.96 | .28752 | 213.1 | 1.3277 |
| 583 | 34.546 | 1.0111 | −104.84 | .3088 | 208.1 | 1.3135 |
| 595 | 34.591 | .99898 | −101.61 | .27344 | 203.5 | 1.2998 |
| 607 | 34.638 | .98697 | −97.732 | .28266 | 199 | 1.2865 |
| 619 | 34.682 | .97538 | −94.831 | .30421 | 194.7 | 1.2737 |
| 631 | 34.727 | .9642 | −91.272 | .28993 | 190.6 | 1.2615 |
| 643 | 34.77 | .95346 | −87.011 | .31068 | 186.7 | 1.2495 |
| 655 | 34.813 | .94316 | −83.815 | .30744 | 183 | 1.2382 |
| 667 | 34.856 | .93361 | −79.918 | .27943 | 179.6 | 1.2274 |
| 679 | 34.896 | .92397 | −76.514 | .30012 | 176.2 | 1.2169 |
| 691 | 34.937 | .9151 | −73.599 | .28309 | 173.1 | 1.207 |
| 703 | 34.978 | .90644 | −69.409 | .29067 | 170.1 | 1.1975 |
| 715 | 35.018 | .89828 | −66.33 | .28422 | 167.3 | 1.1885 |
| 727 | 35.057 | .89065 | −62.562 | .2659 | 164.7 | 1.1801 |
| 739 | 35.095 | .88326 | −59.956 | .25875 | 162.2 | 1.1722 |
| 751 | 35.134 | .87641 | −56.646 | .23868 | 159.9 | 1.1646 |
| 763 | 35.172 | .86951 | −53.91 | .24354 | 157.6 | 1.1573 |
| 775 | 35.209 | .86346 | −51.105 | .22194 | 155.6 | 1.1506 |
| 787 | 35.245 | .85738 | −48.266 | .21282 | 153.6 | 1.144 |
| 799 | 35.283 | .85188 | −45.993 | .20338 | 151.8 | 1.138 |
| 811 | 35.318 | .84634 | −43.695 | .19372 | 150 | 1.1322 |
| 823 | 35.353 | .84139 | −41.343 | .19689 | 148.4 | 1.1268 |
| 835 | 35.389 | .83641 | −38.968 | .2 | 146.8 | 1.1217 |
| 847 | 35.423 | .83203 | −36.542 | .1891 | 145.4 | 1.117 |
| 859 | 35.457 | .82763 | −34.095 | .17801 | 144 | 1.1125 |
| 871 | 35.491 | .82385 | −32.266 | .1527 | 142.8 | 1.1083 |
| 883 | 35.525 | .82004 | −30.423 | .1411 | 141.6 | 1.1045 |
| 895 | 35.557 | .81654 | −29.213 | .14287 | 140.5 | 1.1007 |
| 907 | 35.59 | .81303 | −27.322 | .13053 | 139.4 | 1.0974 |
| 919 | 35.623 | .80982 | −25.409 | .14584 | 138.4 | 1.094 |
| 931 | 35.655 | .80693 | −24.158 | .11908 | 137.5 | 1.091 |
| 943 | 35.687 | .80435 | −22.213 | .10627 | 136.7 | 1.0885 |
| 955 | 35.719 | .80143 | −21.606 | .10726 | 135.8 | 1.0858 |
| 967 | 35.751 | .79916 | −20.308 | .094208 | 135.1 | 1.0834 |
| 979 | 35.782 | .79656 | −19.009 | .10904 | 134.3 | 1.0812 |
| 991 | 35.812 | .7946 | −17.691 | .095525 | 133.7 | 1.0792 |
| 1003 | 35.842 | .79231 | −16.372 | .096291 | 133 | 1.0772 |
| 1015 | 35.871 | .79067 | −15.722 | .082606 | 132.5 | 1.0755 |
| 1027 | 35.901 | .7887 | −14.387 | .083251 | 131.9 | 1.0739 |
| 1039 | 35.931 | .78705 | −13.726 | .08362 | 131.4 | 1.0724 |
| 1051 | 35.959 | .7854 | −12.376 | .069766 | 130.9 | 1.071 |
| 1063 | 35.988 | .78408 | −11.709 | .070063 | 130.5 | 1.0699 |
| 1075 | 36.018 | .78276 | −11.039 | .056074 | 130.1 | 1.0687 |
| 1087 | 36.046 | .78143 | −10.363 | .056326 | 129.7 | 1.0677 |
| | | ## OXIDATION COMPLETE ## | | | | |
| | | TOC = 129.7 PPB | | | | |

Figure 15:
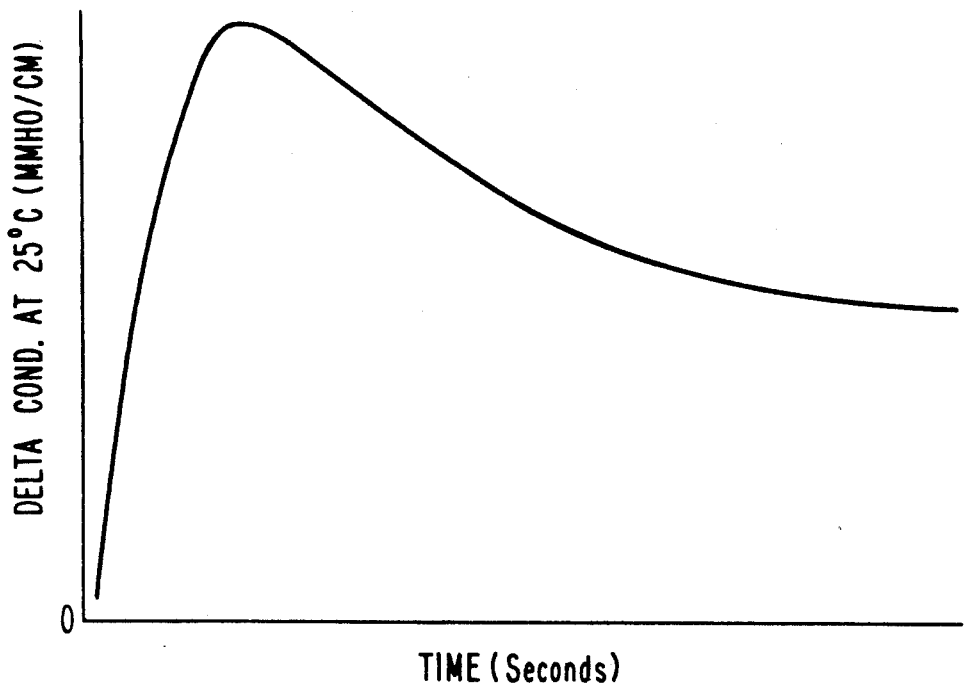
FIGS. 15–17 show actual test results.
Figure 16:
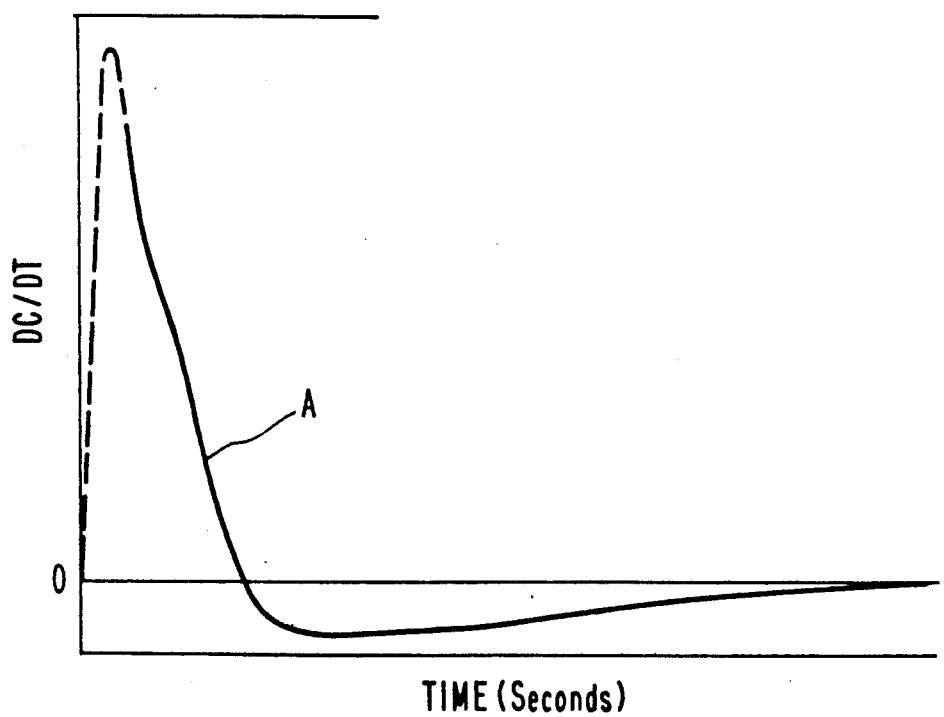
Figure 17:
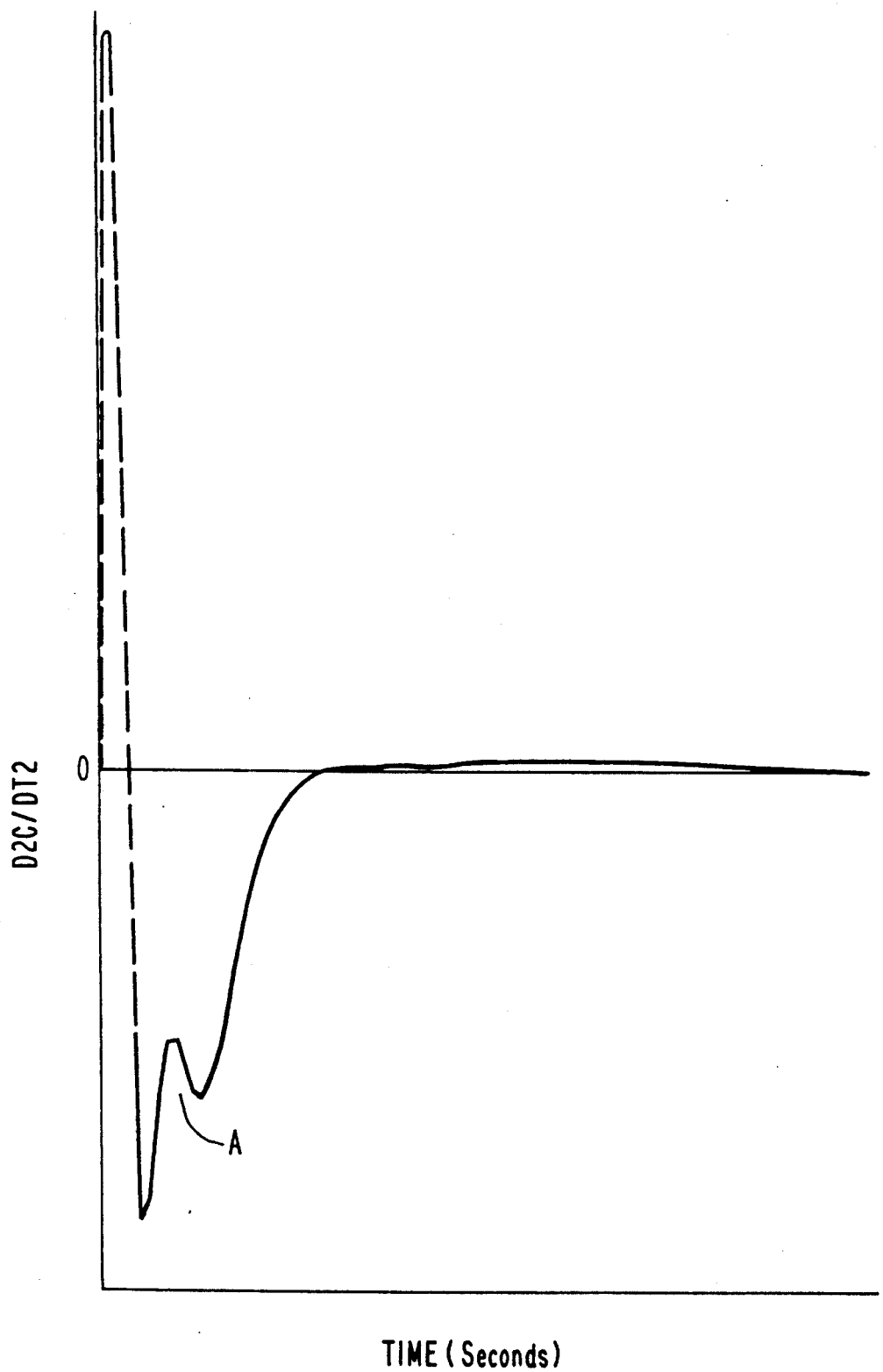

FIGS. 15, 16 and 17 show the data of Example II, plotting respectively conductivity and the first and second time derivatives thereof. The dotted lines in FIGS. 16 and 17 were added by interpolation; as mentioned, data for the first few values of the first and second derivatives are not calculated by the computer program used to generate the data of Example II and the remainder of the plots of FIGS. 16 and 17. The characteristic Case III shape is very clear. The extra peak at A in FIG. 17 correctly reflects the additional inflection points at A of FIG. 16. These are believed due to local thermal variations or the like. The contaminant used for this test was acetone, supplied in the amount of 129.7 parts per billion; and the results indicated in Example II show that this result was correctly obtained.

It will be appreciated that there has been described an instrument for measurement of the total organic carbon content of water. As discussed, accurate measurement of the total organic content requires compensation for temperature-induced changes in conductivity since conductivity varies very strongly in dependence on temperature, as described in the article by Poirier et al referred to above. Further, it will be appreciated that measurement of the conductivity of water caused by oxidation of total organic matter is made possible according to the instrument of the invention by its ability to differentiate separation of the change in conductivity occasioned by oxidation of the organic matter to carbon dioxide from the conductivity of the water prior to oxidation and from the instrument contribution. Therefore, the residual conductivity, that is, as measured in Phase I of the plot of FIG. 13, is an indication of the ionic conductivity of the water. Hence, the instrument of the invention, as already described, is effectively an instrument for measuring ionic conductivity and sample temperature as well as total organic carbon content, and it should be appreciated that such a three-function instrument explicitly providing this output data is within the scope of the claims of this application.

Reference has been made throughout this application to measurement of the conductivity between the electrodes of the cell. This must be accomplished with accuracy. Those skilled in the art will recognize that this is not necessarily a simple task. According to the preferred embodiment of the invention, this is accomplished as discussed in co-pending application of Frederick K. Blades, Ser. No. 689,871, filed Jan. 9, 1985, now U.S. Pat. No. 4,683,435. As discussed above, according to the present invention, the sample cell, in which conductivity is measured, is also the cell in which the ultraviolet irradiation and oxidation take place. Those skilled in the art will recognize that when ultraviolet radiation falls upon the electrodes (as desired according to the present invention, to eliminate fouling and the like) the photoelectric and photoionic effects will cause the cell to act as a battery, effectively impressing a DC voltage across the electrodes. This biases the AC signal which is conducted through the sample, and appropriate correction must be made. For reasons discussed in the co-pending application of Blades referred to above, simple filtering of the DC component is not possible.

According to the preferred embodiment, and as discussed in the co-pending application of Blades, the cell is used in an active feedback loop which generates a DC voltage to compensate for the "battery voltage" impressed between the cell electrodes. The AC signal placed on one electrode, transmitted through the water sample and detected on the other electrode is similarly compensated for nonlinearities caused by other circuit elements, to provide a linear output with respect to conductivity across the cell.

As discussed above, the time for the oxidation reaction to go to completion is typically a matter of minutes, sometimes as many as ten to twenty, depending on the contaminant involved, the intensity of the radiation and other variables. It would clearly be desirable to provide a system in which total organic carbon content of a water stream could be monitored substantially continuously, i.e. in "real time", so that for example an alarm could be triggered if a sudden change in the organic content was detected. FIG. 18 shows an apparatus for so doing. This apparatus comprises two of the cells of FIGS. 11 and 12 in series, a first cell 100 upstream without an ultraviolet lamp and a second cell 102 downstream with a continuously-running ultraviolet lamp and monitoring the conductivity signals provided by both pairs of electrodes. A flow restrictor 104 is installed upstream such that the flow rate is maintained constant and relatively slow, e.g. 0.2 liters per minute. The upstream cell 100 is mechanically and electrically identical to that described in connection with FIGS. 11 and 12, but because the first cell has no lamp, no oxidation of total organic carbon takes place. Hence, the output of this cell is indicative of the background ionic conductivity of the sample. The second cell 102 is as described above in connection with FIG. 11, and the lamp is continuously turned on. Partial oxidation of the organic materials leads to generation of some $CO_2$ and/or conductive organic intermediaries, and hence to a net change in conductivity. Accordingly, the difference in the conductivity signals from the two cells is indicative of the amount of total organic carbon in the water sample even though it is not fully oxidized during its short residence time in the downstream cell. Thus, while it would not be appropriate to rely on the signal from the second cell for an absolute value of the total organic carbon content of the water stream, the difference between the two signals can be monitored, and any sudden changes in the value of the difference are indicative of sudden changes in the organic content of the stream, which will typically be cause for alarm. Further, at these or other times, of course, the second cell can be used in the mode described above, i.e. for an extended run to determine the actual level of organics in the system, simply by shutting a valve downstream of the second cell and monitoring the oxidation reaction to completion.

It will be appreciated that because the organics in the continuously flowing stream are only partially oxidized, the amount of change in conductivity resulting from said partial oxidation is dependent on the sample flow rate. Therefore, to obtain repeatable results, either a means to maintain the flow rate constant or a means to measure the sample flow rate, and therefore compensate the signal accordingly, must be employed.

It will be further appreciated that there will be a tendency for the electrodes of the first cell, that without an ultraviolet lamp, to foul with time and that this will affect the accuracy of the background measurements. This can be corrected for by compensation of the background value by periodically turning off the light on the second cell, the electrodes of which will have been kept clean by ultraviolet radiation, and adjusting the value provided by the first cell to equal that of the second, providing appropriate compensation for results received thereafter. Alternatively an ultraviolet lamp could be provided for the first cell and operated intermittently to "burn off" any accumulated organics.

We claim:

1. An apparatus for the measurement of total organic carbon contained in a sample of deionized water, comprising:

a sample cell for containing a sample of deionized water;

a source of ultraviolet radiation of a frequency which promotes oxidation of organic carbon compounds disposed such that radiation from said source is incident on said sample cell;

a pair of electrodes in said cell;

means for monitoring the electrical conductivity between said electrodes;

means for measuring the temperature of water in the cell; and means for correcting the monitored conductivity as a function of the measured temperature;

wherein the exposure of a sample of water containing organic carbon compounds to ultraviolet radiation and the monitoring of the consequent change of electrical conductivity of the sample both take place in said sample cell.

2. An apparatus according to claim 1 wherein said sample cell comprises an inlet port for connection to a pressurized source of water to be analyzed and an outlet port for connection to a valve for controlling flow through said cell, such that when said valve is closed a static water sample is effectively defined.

3. An apparatus according to claim 1 wherein the sample cell comprises a window made from material which is substantially transparent to ultraviolet radiation.

4. An apparatus according to claim 3 wherein the source of ultraviolet radiation is disposed in juxtaposition to said window.

5. An apparatus according to claim 1 wherein the source of ultraviolet radiation is an ultraviolet lamp.

6. An apparatus according to claim 5 wherein the ultraviolet lamp is constructed so as to radiate of substantially 184 nanometers wavelength.

7. An apparatus according to claim 1 wherein said means for monitoring the conductivity of water between said electrodes comprises controller means connected to said electrodes, so as to measure the conductivity of said water sample prior to oxidation of organic material, to monitor the temperature of said water sample during said oxidation, and to distinguish between changes in conductivity due to oxidation of organic material, changes in conductivity due to variation in temperature, and changes in conductivity due to instrument contribution, whereby said total organic carbon content can be identified separately from nonorganic ionic concentration, from instrument contribution and from changes in conductivity due to variation in temperature.

8. An apparatus according to claim 7 wherein said controller means is constructed so as to distinguish between changes in conductivity due to oxidation of organic carbon to carbon dioxide and other changes in conductivity by monitoring the first and second time derivatives of conductivity and determining when either of said first and second time derivatives becomes linear, indicating that said oxidation reaction is complete.

9. An apparatus according to claim 1 further comprising means for determining when an output signal provided by said means for monitoring the electrical conductivity indicates that the oxidation reaction has been substantially completed, for determining the contribution made to the conductivity of the sample due to sources other than carbon dioxide resulting from oxidation of said organic carbon compounds, and means for determining the total organic carbon content of said sample as a function of the change in conductivity of said water sample during completion of said reaction.

10. An apparatus according to claim 9 wherein said means for determining when said reaction is completed comprises means for monitoring the first and second time derivatives of said conductivity and for determining when either of said derivatives is substantially equal to zero, indicating that further change in the conductivity thereafter is linear.

11. An apparatus according to claim 10 wherein said means for determining the contribution made to the conductivity of the sample, other than by said carbon dioxide, comprises means for measuring the initial conductivity of the sample prior to commencement of oxidation, and means for multiplying the first time derivative of the conductivity at a time T, when the second time derivative of conductivity becomes substantially zero, by said time T, and substracting the resultant quantity and the initial conductivity from the total conductivity measured at time T, whereby the remainder is proportional to the conductivity contribution made by carbon dioxide generated by oxidation of organic material in said water sample.

12. An apparatus according to claim 1, further comprising means for determining when said conductivity or a time-rate of change of said conductivity has reached a stable value, indicating that oxidation of said organic carbon compounds due to said ultraviolet light being incident thereon has been substantially completed.

13. An apparatus according to claim 12 wherein said means for determining when said conductivity or said time-rate of change said conductivity has reached a stable value indicating that said oxidation has been substantially completed comprises means for monitoring the first and second time derivatives of the conductivity measured between said electrodes and means for determining when the second derivative of said conductivity has substantially reached zero.

14. An apparatus according to claim 13 wherein said means for monitoring the first and second time derivatives of the conductivity includes means for determining if said second derivative approaches zero from negative values and for determining from the sign of the first time derivative of the conductivity whether said second time derivative is approaching its asymptotic limit.

15. An apparatus according to claim 14 wherein said means for monitoring conductivity further comprises means for analyzing ones of a plurality of samples in a succession of runs such that, if in a given analytic run, the sign of the first time derivative indicates that the second time derivative of the conductivity is not approaching its asymptotic limit, said means for monitoring conductivity compares the peak value of the conductivity reached in the given run with the peak value reached in one or more preceding runs, and if said peak values are substantially equal, indicates that the total organic carbon level of the water samples has not changed substantially from run to run.

16. An apparatus according to claim 13 further comprising means for correcting the conductivity measured to an absolute value comprising means for measuring the initial conductivity of the water sample prior to oxidation and means for multiplying the first time derivative of the conductivity at a time T, when the second time derivative has substantially reached zero, by said time T and substracting the resulting quantity and the initial conductivity from the total conductivity measured between said electrodes at said time T, to provide a compensated output signal representative of the change in conductivity of the water sample due to oxidation of organic carbon compounds therein.

17. An apparatus according to claim 1 further comprising means for conversion of said compensated output signal indicative of the conductivity of said water sample due to oxidation of carbon compounds to a signal indicative of organic carbon content of said water prior to exposure thereof to ultraviolet radiation.

* * * * *